United States Patent [19]

Strupczewski

[11] Patent Number: 5,134,236
[45] Date of Patent: Jul. 28, 1992

[54] PHENYLHYDRAZONES AS INTERMEDIATES 1-PHENYL-3-(1-PIPERAZENYL)-1H-INDAZOLES

[75] Inventor: Joseph T. Strupczewski, Flemington, N.J.

[73] Assignee: Hoechst-Roussel Pharmaceuticals Incorporated, Somerville, N.J.

[21] Appl. No.: 589,237

[22] Filed: Sep. 28, 1990

Related U.S. Application Data

[60] Division of Ser. No. 289,065, Dec. 23, 1988, Pat. No. 4,999,356, which is a continuation-in-part of Ser. No. 82,760, Aug. 7, 1987, abandoned.

[51] Int. Cl.$^5$ .............. C07D 295/125; C07D 295/185
[52] U.S. Cl. .................. 544/389; 544/371; 544/392; 544/398; 544/402
[58] Field of Search ............. 544/389, 392, 398, 402, 544/371

[56] References Cited

U.S. PATENT DOCUMENTS

| 3,786,094 | 1/1974 | Perronnet et al. | 544/165 |
| 4,954,503 | 9/1990 | Strupczewski et al. | 544/371 |
| 4,957,916 | 9/1990 | Kennis et al. | 514/254 |
| 4,999,356 | 3/1991 | Strupczewski | 544/371 |
| 5,015,740 | 5/1991 | Kennis et al. | 544/366 |

OTHER PUBLICATIONS

Hackler et al, *J. Agric. Food Chem.* 38 p. 508 (1990).

Primary Examiner—Mukund J. Shah
Assistant Examiner—E. Bernhardt
Attorney, Agent, or Firm—E. Korsen

[57] ABSTRACT

Novel 1-phenyl-3-(1-piperazinyl)-1H-indazoles, intermediates and processes for the preparation thereof, and methods for alleviating pain, treating convulsions, and treating depression utilizing compounds or compositions thereof are disclosed.

3 Claims, No Drawings

PHENYLHYDRAZONES AS INTERMEDIATES 1-PHENYL-3-(1-PIPERAZENYL)-1H-INDAZOLES

This is a division of application Ser. No. 289,065 filed Dec. 23, 1988 now U.S. Pat. No. 4,999,356, which is a continuation-in-part of application Ser. No. 082,760, filed Aug. 7, 1987, now abandoned, for 1-Phenyl-3-(1-Piperazinyl)-1H-Indazoles by Joseph T. Strupczewski. The entire disclosure of the related, copending application is relied upon and incorporated by reference herein.

This invention relates to 1-phenyl-3-(1-piperazinyl)1H-indazoles. More particularly, this invention relates to 1-phenyl-3-(1-piperazinyl)-1H-indazoles of the formula:

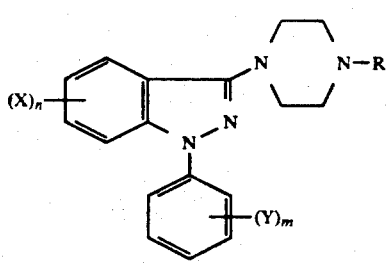

FORMULA I wherein n is an integer having a value of 0 or 1; m is an integer having a value of 0 to 2, inclusive; X and Y are independently selected from the group consisting of halogen, loweralkyl, loweralkoxy, loweralkylthio, diloweralkylamino, loweralkylamino, amino, nitro, cyano, mercapto, hydroxy, and trifluoromethyl, wherein for each value of m, Y may be the same or different; and R is selected from the group consisting of hydrogen, loweralkyl, cycloalkylloweralkyl, loweralkenyl, hydroxyloweralkyl, diloweralkylaminoloweralkyl, diloweralkylphosphinylloweralkyl, cyano, loweralkoxycarbonyl, loweralkanoyl, aminocarbonyl, loweralkylaminocarbonyl, and

wherein q is an integer having a value of 0 to 5, inclusive, $X^1$ is selected from the group consisting of halogen, loweralkyl, loweralkoxy, loweralkylthio, diloweralkylamino, loweralkylamino, amino, nitro, cyano, mercapto, hydroxy, and trifluoromethyl, and p is an integer having a value of 0 to 5, inclusive, $X^1$ is selected from the group consisting of halogen, loweralkyl, loweralkoxy, loweralkylthio, diloweralkylamino, loweralkylamino, amino, nitro, cyano, mercapto, hydroxy, and trifluoromethyl, and p is an integer having a value of 0 to 2 inclusive, wherein for each value of p, $X^1$ may be the same or different; the geometrical isomers, optical antipodes or pharmaceutically acceptable acid addition salts thereof, which are useful for alleviating pain, treating convulsions, and treating depression, alone or in combination with inert adjuvants.

Preferred 1-phenyl-3-(1-piperazinyl)-1H-indazoles of this invention are those Formula I compounds wherein R is selected from the group consisting of hydrogen, loweralkyl, cycloalkylloweralkyl, loweralkenyl, loweralkanoyl, diloweralkylphosphinylloweralkyl, aminocarbonyl, loweralkylaminocarbonyl, and diloweralkylaminoloweralkyl. Most preferred 1-phenyl-3-(1-piperazinyl)-1H-indazoles are those Formula I compounds wherein R is hydrogen or loweralkyl.

Subgeneric to the 1-phenyl-3-(1-piperazinyl)-1H-indazoles of this invention are Formula I compounds wherein:

(a) R is hydrogen, loweralkyl, loweralkenyl, or cycloalkylloweralkyl;
(b) R is

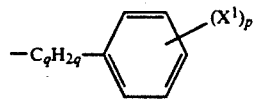

wherein q is an integer having a value of 0 to 5, inclusive, $X^1$ is selected from the group consisting of halogen, loweralkyl, loweralkoxy, loweralkylthio, diloweralkylamino, loweralkylamino, amino, nitro, cyano, mercapto, hydroxy, and trifluoromethyl, and p is an integer having a value of 0 to 2, inclusive, wherein for each value of p, $X^1$ may be the same or different;

(c) R is cyano;
(d) R is hydroxyalkyl;
(e) R is diloweralkylaminoloweralkyl;
(f) R is diloweralkylphosphinylloweralkyl;
(g) R is loweralkoxycarbonyl;
(h) R is aminocarbonyl or loweralkylaminocarbonyl;
(i) R is loweralkanoyl;
(j) m is 0 or 1;
(k) Y is fluorine or chlorine; and
(l) Y is trifluoromethyl.

In a further embodiment, this invention relates to 1-[(phenylhydrazono)(phenyl)methyl]piperazines of the formula:

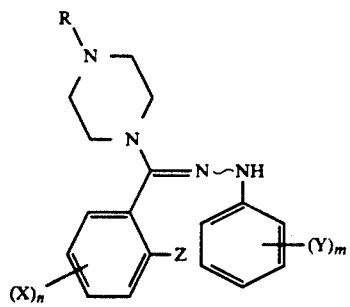

Formula II wherein R is selected from the group consisting of loweralkyl, loweralkoxycarbonyl, and

wherein $X^1$ is selected from the group consisting of halogen, loweralkyl, loweralkoxy, loweralkylthio, diloweralkylamino, nitro, cyano, and trifluoromethyl, and p is an integer having a value of 0 to 2 inclusive, wherein for each value of p, $X^1$ may be the same or different; X and Y are independently selected from the group consisting of halogen, loweralkyl, loweralkoxy, loweralkylthio, diloweralkylamino, nitro, cyano, and trifluoromethyl; n is an integer having a value of 0 or 1; m is an integer having a value of 0 to 2, inclusive; wherein for each value of m, Y may be the same or different; and Z is fluorine; the geometrical isomers, optical antipodes, or pharmaceutically acceptable acid addition salts thereof.

Subgeneric to the 1-[(phenylhydrazono)(phenyl)methyl]piperazines of Formula II are those compounds wherein R is loweralkyl, loweralkoxycarbonyl, or phenyl.

As used throughout the specification and appended claims, the following definitions shall apply:

"Loweralkyl"—a linear or branched, acyclic hydrocarbon radical containing no unsaturation and having the formula $-C_xH_{2x+1}$ wherein x is an integer having a value of 1 to 7 inclusive, such as methyl, ethyl, 1-propyl, 2-propyl, 1-butyl, 1-pentyl, 2-pentyl, 3-hexyl, 4-heptyl, and the like. Preferred loweralkyls are those radicals wherein x has a value of 1 to 3 inclusive, most preferably 1 or 2.

"Loweralkenyl"—a linear or branched, acyclic hydrocarbon radical having one olefinic bond and represented by the formula: $-C_xH_{2x-1}$, wherein x is an integer having a value of 3 to 7 inclusive, such as 2-propenyl, 3-butenyl, 3-pentenyl, 3-hexenyl, 6-heptenyl, and the like. Preferred loweralkenyls are those radicals wherein x has a value of 3 to 5 inclusive, and, most preferably, is 3.

"Cycloalkyl"—a cyclic hydrocarbon radical of the formula $-C_xH_{2x-1}$ wherein x has a value of 3 to 7 inclusive, such as cyclopropyl, cyclobutyl, cyclopentyl, cyclohexyl, and cycloheptyl. Preferred cycloalkyls are those radicals wherein x has a value of 3 to 6 inclusive, and, most preferably, is 3.

"Loweralkoxy"—an acyclic organic radical of the formula $-OC_xH_{2x+1}$ wherein x is an integer having a value of 1 to 7 inclusive, such as methoxy, ethoxy, 1-and 2-propoxy, 1,2-dimethylethoxy, 1-butoxy, 1- and 2-pentoxy, 3-hexoxy, 4-heptoxy and the like. Preferred loweralkoxys are those radicals wherein x has a value of 1 to 5 inclusive, most preferably, 1 to 3 inclusive.

"Loweralkylthio"—an acyclic organic radical of the formula $-SC_xH_{2x+1}$ wherein x is an integer having a value of 1 to 7 inclusive, such as methylthio, ethylthio, 1-and 2-propylthio, 1-butylthio, 1- and 2-pentylthio, 3-hexylthio, 4-heptylthio, and the like. Preferred loweralkylthios are those radicals wherein x has a value of 1 to 3 inclusive and, most preferably, is 1 or 2.

"Loweralkoxycarbonyl"—an acyclic organic radical of the formula $-C(O)OC_xH_{2x+1}$ wherein x is an integer having a value from 1 to 5 inclusive, such as methoxycarbonyl, ethoxycarbonyl, 1- and 2-propoxycarbonyl, 1-butoxycarbonyl, 1- and 2-pentoxycarbonyl and the like. Preferred loweralkoxycarbonyls are those radicals wherein x has a value of 1 to 4 inclusive, and most preferably, is 1 or 2.

"Halogen"—a member of the group consisting of fluorine, chlorine, bromine or iodine radicals. Preferred halogens are fluorine or chlorine radicals.

"Loweralkylamino"—an acyclic organic radical of the formula

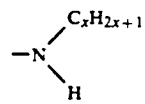

wherein x is an integer having a value of 1 to 7 inclusive, such as methylamino, ethylamino, 2-propylamino, 1-butylamino, 2-pentylamino, 3-hexylamino, 1-heptylamino, and the like. Preferred loweralkylaminos are those radicals wherein x has a value of 1 to 3 inclusive, and most preferably is 1.

"Diloweralkylamino"—an acyclic organic radical of the formula

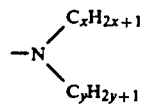

wherein x and y are independently integers having values of 1 to 7 inclusive, such as dimethylamino, diethylamino, N,N-methylethylamino, N,N-di(2-propyl)amino, N,N-di(1-butyl)amino, N,N-di(2-pentyl)amino, N,N-di(3-hexyl)amino, N,N-di(1-heptyl)amino, and the like. Preferred diloweralkylaminos are those radicals wherein x and y have values of 1 to 3 inclusive, and most preferably, are 1.

"Diloweralkylphosphinylloweralkyl"—an acyclic organic radical of the formula

wherein x and y are independently integers having values of 1 to 7 inclusive, and z is an integer having a value of 2, wherein for each z, y may be the same or different, such as (dimethyl)phosphinylmethyl, (dimethyl)phosphinylethyl, (diethyl)phosphinylmethyl, di(2-propyl)phosphinylmethyl, di(1-butyl)phosphinylmethyl, di-(2-pentyl)phosphinylmethyl, di(3-hexyl)phosphinylethyl, di(1-heptyl)phosphinylethyl, and the like. Preferred diloweralkylphosphinylloweralkyls are those radicals wherein x and y have values of 1 or 2, and most preferably are 1.

"Loweralkanoic acid"—a compound formed by the combination of a carboxyl group with a hydrogen atom or a loweralkyl as previously defined Examples of loweralkanoic acids are formic, acetic, propionic, 2,2-dimethylacetic, pentanoic, hexanoic, heptanoic, octanoic acid, and the like.

"Loweralkanoyl"—a radical formed by the removal of the hydroxyl function from a loweralkanoic acid. Exemplary of such radicals are formyl, acetyl, propionyl, 2,2-dimethylacetyl, pentanoyl, hexanoyl, heptanoyl, octanoyl, and the like. Preferred loweralkanoyls are those radicals formed by the removal of the hydroxyl function from alkanoic acids having up to 2, most preferably 1, carbon atom(s).

"Aminocarbonyl"—an organic radical of the formula $-C(O)NH_2$.

"Loweralkylaminocarbonyl"—an organic radical of the formula

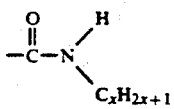

wherein x is an integer having a value of 1 to 7, inclusive. Preferred loweralkylaminocarbonyls are those radicals wherein x has a value of 1 to 3 inclusive, and most preferably is 1.

To prepare the 1-[(phenylhydrazono)(phenyl)methyl]piperazines of Formula II, a phenylhydrazine 1 is condensed with a 2-fluoro- or 2-chlorobenzoyl halide 2 to form a 2-fluoro- or 2-chlorobenzoic acid hydrazide 3 which is converted to a chlorophenylhydrazone 4 and reacted with a piperazine 5, to form a 1-[(phenylhydrazono)(phenyl)methyl]piperazine 6. See Reaction Scheme A.

The condensation of a phenylhydrazine 1 with a 2-chloro or 2-fluorobenzoyl halide 2 is accomplished by conventional methods such as are well known in the art. In general, the phenylhydrazine 1 and benzoyl halide 2 are reacted in the presence of a weakly basic organic solvent at a temperature of from about 0° C. to about 20° C. to form a benzoic acid hydrazide 3. Preferred reaction temperatures are subject to variation depending upon the reactivity of the particular starting materials employed In order to control the rate of reaction between the benzoyl halide 2 and the phenylhydrazine 1, it is recommended that the benzoyl chloride be added to the phenylhydrazine in a dropwise fashion. Among the benzoyl halides there may be mentioned 2-fluorobenzoyl chlorides, 2-chlorobenzoyl chlorides, 2-fluorobenzoyl bromides, and 2-chlorobenzoyl bromides, with 2-fluorobenzoyl chlorides being preferred. Suitable solvents include heterocyclic amines such as pyridine, lutidine, collidine, picoline, and the like. Pyridine is preferred. If desired, the condensation may be conducted in the presence of an inert organic cosolvent such as, a halocarbon, for example, chloroform, methylene chloride, carbon tetrachloride, and the like. The reaction of phenylhydrazine with benzoyl chloride is described for example, in Green, B. et al. *Tetrahedron*, 34, 1633-1639 (1978).

The chlorination of the benzoic acid hydrazide 3 is well known in the art and is described for example, in Huisgen, R. et al. *Tetrahedron*, 17, 3, 18 (1962). Among the chlorinating agents there may be mentioned phosphorous oxychloride, phosphorous pentachloride, and the like Phosphorous pentachloride is preferred. Among the solvents suitable for the chlorination reaction are etheral solvents such as 1,2-dimethoxyethane, bis(2-methoxyethyl) ether, diethyl ether, tetrahydrofuran and the like; inert halocarbons such as chloroform, carbon tetrachloride, methylene chloride, and the like, and mixtures thereof. Diethyl ether is preferred. Recommended temperatures for the reaction of the benzoic acid hydrazide 3 with the chlorinating agent range from about 30° C. to about 100° C., with temperatures of from about 30° C. to about 65° C. being preferred. Upon completion of the reaction it is generally desirable to treat the reaction medium with an ethereal solution of phenol in order to generate the chlorophenylhydrazone 4 from the phosphorous-containing intermediate.

Alternatively, the chlorophenylhydrazone 4 can be produced by reacting the benzoic acid 3 with triphenylphosphine and a carbon tetrahalide (e.g. carbon tetrachloride, carbon tetrabromide, and the like, carbon tetrachloride being preferred). The reaction is ordinarily conducted under anhydrous conditions at a temperature of from about 20° C. to about 80° C., preferably from about 20° C. to about 50° C. in a solvent such as acetonitrile.

The reaction of a chlorophenylhydrazone 4 with a piperazine 5 to produce a 1-[(phenylhydrazono)(phenyl)methyl]piperazine 6 is generally conducted neat or in the presence of an aromatic hydrocarbon, a polar aprotic solvent or an ethereal solvent at a temperature of from about 20° C. to about 100° C. Among the suitable solvents are benzene, toluene, xylene, dimethylformamide, dimethylacetamide, dimethylsulfoxide, hexamethylphosphoramide, diethyl ether, dioxane, 1,2-dimethoxyethane, bis(2-methoxyethyl)ether, tetrahydrofuran and the like, with tetrahydrofuran being preferred. Preferred reaction temperatures are subject to variation depending, in part, upon the solvent employed The preparation of the 1-phenyl-3-(1-piperazinyl)-1H-indazoles of this invention is illustrated by Reaction Scheme B.

As illustrated, cyclization of a 1-[(phenylhydrazono)(phenyl)methyl]piperazine 6 wherein R is loweralkyl, loweralkoxycarbonyl or phenyl, yields the corresponding indazole 7.

Cyclization is conventionally carried out by treating the 1-[(phenylhydrazono)(phenyl)methyl)]piperazine 6 with an appropriate base such as, for example, an alkali metal hydride, carbonate, or alkoxide. Examplary of the bases suitable for use herein are potassium hydride, sodium hydride, lithium hydride, potassium carbonate, potassium t-butoxide, sodium ethoxide, and the like. Potassium t-butoxide and potassium carbonate are preferred. In general, the cyclization reaction is conducted in the presence of a suitable solvent at a temperature of from about 20° C. to about 120° C. Included among the suitable solvents are ethereal and polar aprotic solvents, ethereal solvents such as, for example, diethyl ether, bis(2-methoxyethyl)ether, tetrahydrofuran, 1,2-dimethoxyethane, dimethylformamide, dimethylacetamide, dimethylsulfoxide and hexamethylphosphoramide. Tetrahydrofuran and dimethylformamide are preferred, with the use of dimethylformamide being recommended when the base is an alkali metal carbonate. Preferred reaction temperatures are subject to variation depending upon factors which include solvent and base selection. For example, when the solvent is tetrahydrofuran and the base is potassium t-butoxide, reaction temperatures of from about 20° to about 65° are preferred, whereas, when the solvent is dimethylformamide and the base is potassium carbonate, a reaction temperature of from about 50° to about 120° C. is preferred.

Formula I compounds wherein R is hydrogen 8 may be prepared by the hydrolysis of 1-phenyl-3-(1-piperazinyl)-1H-indazoles 7 wherein R is loweralkoxycarbonyl. The hydrolysis is conveniently performed in an aqueous alkanol in the presence of an appropriate base. Among the suitable alkanols there may be mentioned ethanol, 1- and 2-propanol, t-butanol, 2-methoxyethanol, and the like. Ethanol and 2-methoxyethanol are preferred. Appropriate bases include alkali metal hydroxides such as, for example, lithium hydroxide, sodium hydroxide and, most preferably, potassium hydroxide. The hydrolysis is generally conducted at temperatures within a range of from about 70° C. to about 125° C.

Alkylation of a Formula I indazole wherein R is hydrogen 8 by treatment with a halide of the Formula $R^1 X^2$ wherein $R^1$ is loweralkyl, cycloalkylloweralkyl, hydroxyloweralkyl, loweralkenyl, diloweralkylphosphinylloweralkyl, or

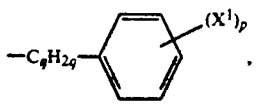

all as previously described, and $X^2$ is halogen, preferably chlorine or bromine, furnishes a 1-piperazinyl-1H-indazole 9 substituted at the 4-position of the piperazinyl ring by $R^1$.

Halides of the formula $R^1X^2$ include loweralkylhalides such as, for example, isopropyl bromide, propyl bromide, ethyl chloride, ethyl bromide and the like, ethyl bromide being preferred; cycloalkylloweralkyl halides such as for example, (bromomethyl)cyclopropane, (bromomethyl)cyclohexane, (chloromethyl)cyclohexane, (chloromethyl)cyclopropane, and the like, (chloromethyl)cyclopropane being preferred; hydroxyloweralkyl halides such as, for example, 3-bromo-1-propanol, 1-bromo-2-propanol, 3-chloro-1-propanol, 1-chloro-2-propanol, 2-chloroethanol, 2-bromoethanol and the like, 2-bromoethanol being preferred; loweralkenyl halides such as, for example, 3-chloro-1-butene, 1-chloro-2-butene, 4-bromo-1-butene, allyl chloride, allyl bromide, and the like, allyl bromide being preferred; diloweralkylphosphinylloweralkyl halides such as, for example, bromomethyl dimethylphosphine oxide, 2-chloroethyl dimethylphosphine oxide, 2-bromoethyl dimethylphosphine oxide, chloromethyl dimethylphosphine oxide and the like, chloromethyl dimethylphosphine oxide being preferred; and halides of the formula

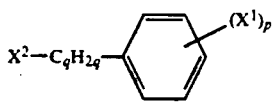

wherein q, p, $X^1$, and $X^2$ are as previously defined such as, for example, benzyl chloride, benzyl bromide, (2-chloroethyl)benzene, (2-bromoethyl)benzene, and the like, (2-bromoethyl)benzene being preferred. The alkylation reaction is conducted in the presence of an alkali metal carbonate or bicarbonate in a suitable inert organic solvent. Among the alkali metal carbonates and bicarbonates suitable for use in the alkylation reaction there may be mentioned sodium carbonate, sodium bicarbonate, potassium carbonate, potassium bicarbonate, lithium carbonate and the like. Potassium carbonate is preferred. Suitable solvents include polar aprotic solvents such as, for example, dimethylformamide, dimethylsulfoxide, dimethylacetamide, hexamethylphosphoramide and the like. Dimethylformamide is the solvent of choice for numerous reactions, solvent preference being determined, in part, by the particular halide reacted. The alkylation is generally conducted at a temperature of from about 50° C. to about 100° C., with temperature ranges of preference being determined in part by the particular halide reacted.

In turn, Formula I compounds wherein R is cyano can be treated with a mineral acid, e.g. H , at a temperature of ranging from 80° C. to reflux of the mixture for a period of from 4 to 24 hours to form compounds of Formula I wherein R is hydrogen.

The introduction of cyano functionality to the 4-position of the piperazinyl ring of the 1H-indazoles of this invention is accomplished by treating a Formula I indazole wherein R is loweralkyl, preferably methyl, with a cyanogen halide, e.g. cyanogen bromide, under the alkylation conditions previously described to yield a (1H-indazol-3-yl)-1-piperazine carbonitrile Preferably, the reaction is conducted at a temperature of about 20°-25° in the presence of potassium carbonate, utilizing dimethylsulfoxide as a solvent.

The introduction of a formyl radical R to the indazoles of this invention is alternatively accomplished by treating a Formula I indazole wherein R is hydrogen with formic acid in the presence of acetic anhydride. The reaction is generally carried out at a temperature of from about 20° C. to about 75° C., preferably from about 50° C. to about 60° C. in the presence of a suitable solvent. Suitable solvents include ethereal solvents such as, for example, diethyl ether, bis(2-methoxyethyl)ether, and tetrahydrofuran. Tetrahydrofuran is preferred.

Similarly, diloweralkylaminoloweralkyl or loweralkanoyl functionality may be introduced to the 4-position of the piperazinyl ring of the 1H-indazoles of the invention by treating a Formula I compound wherein R is hydrogen 8 with an appropriate diloweralkylamino or loweralkanoyl halide (e.g. 2-dimethylaminoethyl chloride, 3-dimethylamino-2-methylpropyl chloride, 2-dimethylaminoisopropyl chloride, acetyl chloride, acetyl bromide, propionyl chloride and the like), under alkylation conditions as previously described.

The 1H-indazoles of this invention can be provided with aminocarbonyl or loweralkylaminocarbonyl functionality at the 4-position of the piperazinyl ring thereof by treating a Formula I compound wherein R is hydrogen with a nitro-substituted urea of the formula

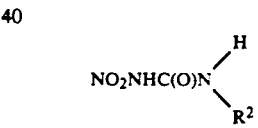

wherein $R^2$ is hydrogen or loweralkyl. The reaction is generally conducted in the presence of a suitable solvent at a temperature of from about 20° C. to about 100° C., preferably from about 80° C. to about 100° C. Suitable solvents include polar aprotic solvents such as, for example, dimethylformamide, dimethylacetamide, dimethylsulfoxide and hexamethylphosphoramide. Dimethylformamide is preferred.

Included among the compounds of this invention are:
3-(4-methyl-1-piperazinyl)-1-phenyl-1H-indazole;
1-phenyl-3-[4-(2-phenylethyl)-1-piperazinyl]-1H-indazole;
1-phenyl-3-[4-phenylmethyl-1-piperazinyl]-1H-indazole;
1-phenyl-3-[4-n-propyl-1-piperazinyl]-1H-indazole;
1-(2-fluorophenyl)-3-(1-piperazinyl)-1H-indazole;
1-(3-fluorophenyl)-3-(1-piperazinyl)-1H-indazole;
1-(2,4-difluorophenyl)-3-(1-piperazinyl)-1H-indazole;
1-(4-fluorophenyl)-3-(4-methyl-1-piperazinyl)-1H-indazole;
3-(4-methyl-1-piperazinyl)-1-[4-(trifluoromethyl)phenyl]-1H-indazole;
1-(4-methoxyphenyl)-3-(1-piperazinyl)-1H-indazole;

1-(4-hydroxyphenyl)-3-(1-piperazinyl)-1H-indazole;
1-(4-nitrophenyl)-3-(1-piperazinyl)-1H-indazole;
1-(4-aminophenyl)-3-(1-piperazinyl)-1H-indazole;
3-[4-(2-hydroxyethyl)-1-piperazinyl]-1-phenyl-1H-indazole;
6-fluoro-1-phenyl-3-(1-piperazinyl)-1H-indazole;
6-fluoro-1-(4-fluorophenyl)-3-(1-piperazinyl)-1H-indazole;
6-fluoro-1-(4-fluorophenyl)-3-(4-methyl-1-piperazinyl)-1H-indazole;
6-fluoro-1-(2-fluorophenyl)-3-(1-piperazinyl)-1H-indazole;
6-fluoro-1-(2-chlorophenyl)-3-(1-piperazinyl)-1H-indazole;
6-chloro-1-phenyl-3-(1-piperazinyl)-1H-indazole;
6-bromo-1-phenyl-3-(1-piperazinyl)-1H-indazole;
5-fluoro-1-phenyl-3-(1-piperazinyl)-1H-indazole;
6-methoxy-1-(4-fluorophenyl)-3-(1-piperazinyl)-1H-indazole;
5-methoxy-1-(4-fluorophenyl)-3-(1-piperazinyl)-1H-indazole;
5-hydroxy-1-(4-fluorophenyl)-3-(1-piperazinyl)-1H-indazole;
5-trifluoromethyl-1-phenyl-3-(1-piperazinyl)-1H-indazole;
5-nitro-1-phenyl-3-(1-piperazinyl)-1H-indazole;
5-amino-1-phenyl-3-(1-piperazinyl)-1H-indazole;
4-(1-phenyl-1H-indazol-3-yl)-1-piperazine carbonitrile;
3-(4-dimethylaminomethyl-1-piperazinyl)-1-phenyl-1H-indazole;
3-(4-(2-dimethylamino)ethyl-1-piperazinyl)-1-phenyl-1H-indazole;
3-(4-allyl-1-piperazinyl)-1-phenyl-1H-indazole; and
3-(4-cyclopropylmethyl-1-piperazinyl)-1-phenyl-1H-indazole.

The 1-phenyl-3-(1-substituted and unsubstituted-piperazinyl)-1H-indazoles of this invention are useful as analgetics due to their ability to alleviate pain in mammals. The procedure employed to determine analgetic utility is a modification of the phenyl-p-benzoquinone writhing assay in mice, a standard assay for analgesia (Proc. Soc. Exptl. Bio. Med., 95 729 (1957)]. In the modified procedure phenyl-p-benzoquinone (Eastman, 12.5 mg) is dissolved in 5 ml of 95% ethanol and the solution is diluted to a total volume of 100 ml with distilled water. The solution is administered to the subject mice subcutaneously at a dose of 10 ml per kg of body weight. A characteristic "writh", an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously at 15, 30, 45 and 60 minutes prior to administration of the phenyl-p-quinone. Four control groups of 2 animals (8 animals) receive an equal volume of the vehicle. After the administration of the phenyl-p-quinone, the mice are placed separately in one liter beakers, and after five minutes, are observed for ten minutes The number of writhes for each animal is recorded. The following formula is used to compute the percent inhibition:

$$\frac{x \text{ Writhes in Control Group} - x \text{ Writhes in Drug Group}}{x \text{ Writhes in Control Group}} \times 100$$

The time period with the greatest percent of inhibition is considered the peak time. A dose range determination is generally reserved for those compounds which inhibit writhing by greater than 65–70% at the screening dose.

A dose range determination is run in the same manner as the time response except 10 animals per group are tested at the peak time of test drug activity. Fifty animals, 4 test drug groups, and a vehicle control are employed. Animals are dosed and tested in a randomized manner. A calculated $ED_{50}$, i.e., the estimated dose at which 50% inhibition of writhing is produced, is determined by a computer linear regression analysis. The calculated subcutaneous (s.c.) dose effecting an approximately 50% inhibition of writhing ($ED_{50}$) in mice produced in this assay is as follows:

| COMPOUND | ANALGESIC ACTIVITY (% Inhibition of Writhing) $ED_{50}$ (mg/kg) |
| --- | --- |
| 1-phenyl-3-(1-piperazinyl)-1H-indazole hydrochloride | 0.7 |
| 1-phenyl-3-(4-methyl-1-piperazinyl)-1H-indazole hydrochloride | 1.6 |
| 4-(1-phenyl-1H-indazol-3-yl)-1-piperazine carbonitrile | 65% @ 20 mg/kg* |
| 4-(1-phenyl-1H-indazol-3-yl)-1-piperazine carboxylic acid ethyl ester | 45% @ 20 mg/kg* |
| 3-[4-(dimethylphosphinylmethyl)-1-piperazinyl]-1-phenyl-1H-indazole | 66% @ 20 mg/kg* |
| 3-[4-(2-propenyl)-1-piperazinyl]-1-phenyl-1H-indazole hydrochloride | 34% @ 20 mg/kg* |
| 1-(4-fluorophenyl)-3-(1-piperazinyl)-1H-indazole | 50% @ 20 mg/kg* |
| 1-(4-fluorophenyl)-3-(4-methyl-1-piperazinyl)-1H-indazole fumarate | 0.8 |
| 4-[1-(4-fluorophenyl)-1H-indazol-3-yl]-1-piperazine carboxylic acid ethyl ester | 58% @ 20 mg/kg* |
| 3-(1-piperazinyl)-1-[4-(trifluoromethyl)phenyl]-1H-indazole hydrochloride | 35% @ 20 mg/kg* |
| 4-[1-(4-(trifluoromethyl)phenyl]-1H-indazol-3-yl]-1-piperazine carboxylic acid ethyl ester | 33% @ 20 mg/kg* |
| 3-(4-cyclopropylmethyl-1-piperazinyl)-1-[4-(trifluoromethyl)phenyl]-1H-indazole | 58% @ 20 mg/kg* |
| 3-[4-(2-phenylethyl)-1-piperazinyl]-1-[4-(trifluoromethyl)phenyl]-1H-indazole hydrochloride | 32% @ 20 mg/kg* |
| 3-[4-(2-hydroxyethyl)-1-piperazinyl]-1-[4-(trifluoromethyl)phenyl]-1H-indazole | 62% @ 20 mg/kg* |
| 1-(2-fluorophenyl)-3-(1-piperazinyl)-1H-indazole hydrochloride | 5.9 |
| propoxyphene (standard) | 3.9 |
| pentazocine (standard) | 1.3 |

*% inhibition of writhing at indicated screening dose, s.c.

Analgesia production is achieved when the 1-phenyl-3-(1-piperazinyl)-1H-indazoles of this invention are administered to a subject requiring such treatment as an effective oral, parenteral or intravenous dose of from 1 to 50 mg/kg of body weight per day. 1-phenyl-3-(1-piperazinyl)-1H-indazoles which achieve effective analgesia production at doses of about 5 mg/kg of body weight per day are particularly desirable. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Several of the 1-phenyl-3-(1-piperazinyl)-1H-indazoles of this invention are also useful as antidepressants by virtue of their ability to elicit an antidepressant response in mammals. Antidepressant activity is demonstrated in the tetrabenazine induced ptosis assay in mice (International Journal of Neuropharmacology, 8, 72 (1969), a standard assay for antidepressant activity.

In this procedure, male mice (Charles River, CD-1), weighing about 20 to 39 g, are used in test groups of five animals. Test compounds are dissolved, or suspended with 1 drop of Tween-80, in distilled water and administered to the animals in volumes of 10 cc per kg of body weight. Tetrabenazine methanesulfonate (76.78% as the free base) is dissolved in distilled water and the concentration of the solution is adjusted so that the dose, administered intraperitoneally (i.p.) to the animals, is 40 mg of tetrabenazine base per kg of animal body weight.

The test compound is administered intraperitoneally (i.p.) or orally to the subject animals, and the tetrabenazine solution is administered 30 minutes or 60 minutes, respectively, thereafter. Tetrabenazine solution and the solvent used to dissolve, or suspend, the test compounds are administered by the same route and at the same intervals as the test compounds to a control group.

The subject animals are placed in individual plastic containers ($10\frac{1}{2}"\times 8"\times 6"$) thirty (i.p.) and sixty minutes (p.o.) after administration of the tetrabenazine solution, and one minute thereafter, the animals are scored for ptosis on the following scale:

| Eye Closure | Score |
| --- | --- |
| Eyes closed | 4 |
| Eyes ¾ closed | 3 |
| Eyes ½ closed | 2 |
| Eyes ¼ closed | 1 |
| Eyes open | 0 |

The total score for each group of 5 animals will therefore vary from 0 to 20; these scores are used as the indications of the activity of the test compound The vehicle-control group score is used as a determinate of the validity of each test. The results are discarded and the test is repeated, if the control score is determined to be less than 17.

A dose range determination is generally reserved for those compounds which inhibit ptosis by greater than about 45–50% at the screening dose.

For calculation of the $ED_{50}$-value of a test compound; i.e., the calculated dose at which the test compound effects a 50% inhibition of tetrabenazine-induced ptosis, four or five doses are administered, and only vehicle-control scores of 17 to 20 are acceptable. A linear-regression analysis is used to estimate $ED_{50}$-values and 95% confidence limits. The intraperitoneal (i.p.) dose effecting a calculated 50% inhibition of ptosis ($ED_{50}$) in mice produced in this assay is as follows:

TABLE 2

| COMPOUND | ANTI-DEPRESSANT ACTIVITY (% Inhibition of Ptosis) $ED_{50}$ (mg/kg, i.p.) |
| --- | --- |
| 1-phenyl-3-(1-piperazinyl)-1H-indazole hydrochloride | 25.4 |
| 1-phenyl-3-(4-methyl-1-piperazinyl)-1H-indazole hydrochloride | 11.1 |
| 1-(4-fluorophenyl)-3-(1-piperazinyl)-1H-indazole | 17.3 |
| 1-(4-fluorophenyl)-3-(4-methyl-1-piperazinyl)-1H-indazole fumarate | 65% @ 20 mg/kg* |
| imipramine (standard) | 1.3 |
| amitriptyline (standard) | 1.5 |

*% inhibition of ptosis at indicated screening dosage (i.p.)

Dosage levels which the 1-phenyl-3-(1-piperazinyl)-1H-indazoles of this invention achieve an antidepressant response is subject to variation depending upon the particular compound employed. In general, antidepressant response may be elicited at effect doses ranging from about 0.01 to about 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

The compounds of the invention are also useful as anticonvulsants due to their anticonvulsant activity in mammals. Anticonvulsant activity is measured in the male mouse using the supramaximal electroshock (SES) assay described in *Arch. Int. Pharmacodyn.* 92: 97–107, 1952. In this procedure groups of animals are used. Drugs are prepared using distilled water and, if insoluble, a surfactant is added. Control animals receive vehicle. Drugs are routinely administered intraperitoneally (i.p.). The dosage volume is 10 ml/kg. A primary screen is given a 30 minute pretreat. The animal's eyes are placed across the output terminals of an A.C. shocker that delivers 206 volts rms for 300 msec. Electrode paste coats the animals eyes at the point of contact with the terminals. A compound is considered to give protection if the mouse does not exhibit extensor tonus. Protection is expressed as normalized percent inhibition relative to vehicle control.

A time response is carried out using six animals/group. Animals are tested at 30, 60 and 120 minutes post drug. Additional time periods are tested if indicated by previous tests. When the peak activity time has been determined, a dose response is initiated using 10 animals/group at that time period. The $ED_{50}$ and 95% confidence interval are calculated by computer probit analysis. The anticonvulsant activity of several of the compounds of this invention is provided in Table 3.

TABLE 3

| COMPOUND | ANTICONVULSANT ACTIVITY (% Inhibition of Convulsion) $ED_{50}$ (mg/kg, i.p.) |
| --- | --- |
| 1-phenyl-3-(1-piperazinyl)-1H-indazole hydrochloride | 100% @ 60 mg/kg* |
| 1-phenyl-3-(4-methyl-1-piperazinyl)-1H-indazole hydrochloride | 14.6 |
| 3-[4-(dimethylphosphinylmethyl)-1-piperazinyl]-1-phenyl-1H-indazole | 24.3 |
| 1-(4-fluorophenyl)-3-(4-methyl- | 12.9 |

TABLE 3-continued

| COMPOUND | ANTICONVULSANT ACTIVITY (% Inhibition of Convulsion) ED$_{50}$ (mg/kg, i.p.) |
|---|---|
| 1-piperazinyl)-1H-indazole fumarate | |
| 3-(4-methyl-1-piperazinyl)-1-[4-(trifluoromethyl)phenyl]-1H-indazole fumarate | 27.0 |
| 3-(4-ethyl-1-piperazinyl)-1-[4-(trifluoromethyl)phenyl]-1H-indazole fumarate | 8.2 |
| 4-[1-(2-chlorophenyl)-1H-indazol-3-yl]-1-piperazine carboxamide hemifumarate | 38.9 |
| 4-[1-(4-fluorophenyl)-1H-indazol-3-yl]-1-piperazine carboxamide | 22.7 |
| phenobarbitol | 8.4 |
| 1-(2-fluorophenyl)-3-(1-piperazinyl)-1H-indazole hydrochloride | 14.7 |
| 1-(4-methylphenyl)-3-(4-methyl-1-piperazinyl)-1H-indazole hydrochloride | 36.1 |
| 1-(4-methoxyphenyl)-3-(4-methyl-1-piperazinyl)-1H-indazole | 12.6 |
| 4-[1-(2-fluorophenyl)-1H-indazol-3-yl]-1-piperazine carboxamide hemifumarate | 38.3 |
| 1-(4-methoxyphenyl)-3-(1-piperazinyl)-1H-indazole hydrochloride | 14.2 |
| 1-(2,4-dichlorophenyl)-3-(4-methyl-1-piperazinyl)-1H-indazole | 42.0 |

*% inhibition of convulsions at indicated dosage.

Anticonvulsant activity is achieved when the compounds of this invention are administered to a subject requiring such treatment at an effective oral, parental or intravenous dose of from 1 to 50 mg/kg of body weight per day. A preferred effective dose within this range is from about 5 to 50 mg/kg of body weight per day. A particularly preferred effective amount is about 20 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or the practice of the invention.

Some compounds within the scope of this invention have greater pharmacological activity in degree or kind than others. For example, the subgeneric group of Formula I compounds wherein R is hydrogen or loweralkyl are more representative of compounds exhibiting analgetic or antidepressant activity. Alternatively, compounds of Formula I wherein R is aminocarbonyl are more representative of compounds exhibiting anticonvulsant activity. These statements of activity are not, however, to be construed as limiting the utility of other compounds defined by Formula I. Further, compounds which are less active, such as those of Formula I wherein R is cyano or alkoxycarbonyl are nevertheless oftentimes desirable as intermediates for the preparation of pharmaceutically more active compounds.

Effective amounts of the present invention may be administered to a subject by any one of various methods, for example, orally as in capsules or tablets, parenterally in the form of sterile solutions or suspensions, and in some cases intravenously in the form of sterile solutions. The 1-phenyl-3-(1-piperazinyl)-1H-indazoles of this invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the preceeding type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and nontoxic in the amounts used.

For the purposes of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzylalcohol or methyl parabens; antioxidants such as ascorbic acid or sodium bisulfite; chelating agents such as ethylenedi-

EXAMPLE 1

4-(1-Phenyl-1H-Indazol-3-yl)-1-Piperazine carboxylic Acid Ethyl Ester

Step 1

To a stirred solution of 50.0 g of phenylhydrazine in 280 ml of dry pyridine, cooled to about 5° was added, dropwise, 80.0 g of o-fluorobenzoyl chloride. After coming to ambient temperature, the reaction mixture was stirred for about 2 hours, and then poured into water. The resultant precipitate was recrystallized from toluene to yield 82 g (77.5%) of 2-fluorobenzoic acid, 2-phenylhydrazide.

Step 2

A mixture of 5.5 g of 2-fluorobenzoic acid, 2-phenylhydrazide, 6.0 g of $PCl_5$ and 20 ml of diethyl ether was refluxed for 1 hour, under nitrogen, and then permitted to stand at ambient temperature for about 20 hours. In the following order, a solution of 5 g of phenol in 5 ml of diethyl ether, 30 ml of methanol, and sufficient water to reach the solution cloud point, were added, dropwise, to the reaction mixture. The mixture was extracted with diethyl ether and the extract washed with water, dried over anhydrous magnesium sulfate, and concentrated in vacuo to an oil. Purification of the oil by means of flash chromatography on silica gel utilizing hexane-ethyl acetate (5%) as the eluent, followed by recrystallization from hexane yielded 1.5 g of α-chloro-2-fluorobenzaldehyde, phenylhydrazone.

Step 3

To 25 ml of stirred, neat ethyl N-piperazinylcarboxylate was added, portionwise, 10.0 g of α-chloro-2-fluorobenzaldehyde, phenylhydrazone. Upon completion of the addition, the reaction mixture was stirred at 90° for five minutes. Dilution of the reaction mixture with water precipitated a gum. The gum was washed with water (2×), and taken up in dichloromethane. The solution was washed with water, brine, dried over anhydrous magnesium sulfate and concentrated to give 17.1 g 4-[(phenylhydrazono)(2-fluorophenyl)methyl]-1-piperazine carboxylic acid ethyl ester.

Step 4

To a stirred solution, under nitrogen of 16.2 g of 4-[(phenylhydrazono)(2-fluorophenyl)methyl]-1-piperazine carboxylic acid ethyl ester in 150 ml of tetrahydrofuran was added, dropwise, a solution of 6.0 g of potassium t-butoxide in 60 ml of tetrahydrofuran. The reaction mixture was stirred at room temperature for 16 hrs., poured into water, and extracted with dichloromethane. The extract was washed with water, dried over anhydrous magnesium sulfate, filtered, and concentrated to an oil. The oil was purified on a Water's Model 500 Preparative High Pressure Liquid Chromatograph utilizing two silica gel columns and hexane/ethyl acetate (3:1 by volume) as the eluent. Concentration of the appropriate fractions yielded 5.3 g (51%) of 4-(1-phenyl-1H-indazol-3-yl)-1-piperazine carboxylic acid ethyl ester.

Analysis for $C_{20}H_{22}N_4O_2$: Calculated: 68.55%C; 6.33%H; 15.99%N. Found: 68.11%C; 6.28%H; 15.93%N.

EXAMPLE 2

1-Phenyl-3-(1-Piperazinyl)-1H-Indazole Hydrochloride

A stirred solution of 6.4 g of 4-(1-phenyl-1H-indazol-3-yl)-1-piperazine carboxylic acid ethyl ester, 6.1 g of potassium hydroxide in 60 ml of water, and 120 ml of ethanol was refluxed under nitrogen for 32 hours. The reaction mixture was concentrated in vacuo, diluted with water, and extracted with diethyl ether. The extract was washed with water and then with brine, dried over anhydrous magnesium sulfate, and concentrated to give 4.4 g of 1-phenyl-3-(1-piperazinyl)-1H-indazole as a solid. The solid was dissolved in ethyl acetate/diethyl ether and treated with ethereal hydrogen chloride to precipitate the hydrochloride salt. Recrystallization from methanol/diethyl ether gave 2.5 g (45%) of 1-phenyl-3-(1-piperazinyl-1H-indazole hydrochloride, mp 265°–267°.

Analysis for $C_{17}H_{18}N_4 \cdot HCl$: Calculated: 64.86%C; 6.08%H; 17.80%N. Found: 64.89%C; 6.15%H; 17.77%N.

EXAMPLE 3

3-[4-(2-Propenyl)-1-Piperazinyl]-1-Phenyl-1H-Indazole Hydrochloride

To a stirred suspension of 5.0 g of 1-phenyl-3-(1-piperazinyl)-1H-indazole and 2.7 g of potassium carbonate in 50 ml of dimethylformamide was added 2.4 g of allyl bromide. The reaction mixture was stirred at 70° C. for 16 hours, poured into water and extracted with ethyl acetate. The extract was washed with water, dried over anhydrous magnesium sulfate, and concentrated to yield 3-[4-(2-propenyl)-1-piperazinyl]-1-phenyl-1H-indazole as an oil. The oil was diluted with diethyl ether and filtered. Treatment of the filtrate with ethereal hydrogen chloride precipitated the hydrochloride salt. Recrystallization from ethanol/diethyl ether gave 2.0 g (21%) of 3-[4-(2-propenyl)-1-piperazinyl]-1-phenyl-1H-indazole hydrochloride, mp 234°–236°.

Analysis for $C_{20}H_{23}N_4 \cdot HCl$: Calculated: 67.69%C; 6.53%H; 15.79%N. Found: 67.33%C; 6.56%H; 15.98%N.

EXAMPLE 4

1-Phenyl-3-(4-Methyl-1-Piperazinyl)-1H-Indazole Hydrochloride

Step 1

To 20 ml of stirred, neat N-methylpiperazine was added, portionwise, 10.0 g of α-chloro-2-fluorobenzaldehyde, phenylhydrazone (prepared as in Step 2 of Example 1). Upon completion of the addition, the reaction mixture was allowed to stand at ambient temperature for 30 minutes. The addition of 200 ml of water to the reaction mixture formed a gum. The gum was washed with water (2×) and taken up in dichloromethane. The solution was washed with water, dried over anhydrous magnesium sulfate and concentrated to give 12.9 g of 1-[(phenylhydrazono)(2-fluorophenyl)methyl]-4-methylpiperazine, as an oil.

--- aminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following Examples are for illustrative purposes only and are not to be construed as limiting the invention. All temperatures are given in degrees centigrade (°C).

Step 2

To a stirred solution, under nitrogen of 12.4 g of 1-[(phenylhydrazono)(2-fluorophenyl)methyl]-4-methylpiperazine in 100 ml of a solution of tetrahydrofuran was added dropwise, 5.3 g of potassium t-butoxide in 50 ml of tetrahydrofuran. Following the addition, the reaction mixture was stirred at ambient temperature for 1 hour, poured into water, and extracted with dichloromethane. The extract was washed with water, dried over anhydrous magnesium sulfate and concentrated to an oil. The oil was purified on a Water's Model 500 Preparative High Pressure Liquid Chromatograph utilizing two silica gel columns and dichloromethane/methanol (4%) as the eluent. Concentration of the appropriate fractions gave 7.0 g (61%) of 1-phenyl-3-(4-methyl-1-piperazinyl)-1H indazole. Treatment of 3.1 g of the indazole with ethereal hydrogen chloride produced the hydrochloride salt. Recrystallization from ethanol gave 2.8 g of 1-phenyl-3-(4-methyl-1-piperazinyl)-1H-indazole hydrochloride, mp 244°-246°.

Analysis for $C_{15}H_{20}N_4 \cdot HCl$: Calculated: 65.74%C; 6.44%H; 17.04%N. Found: 65.78%C; 6.45%H; 16.98%N.

EXAMPLE 5

1-Phenyl-3-(4-Phenyl-1-Piperazinyl)-1H-Indazole

Step 1

To a solution of 6.3 g of α-chloro-2-fluorobenzaldehyde, phenylhydrazone (prepared as in step 2 of Example 1) in 60 ml of tetrahydrofuran was added 19.0 g of N-phenylpiperazine. The reaction mixture was refluxed for 45 mins, cooled, filtered, and concentrated to yield an oil. The oil was titurated with water, taken up in diethyl ether, washed with water, dried over anhydrous magnesium sulfate and concentrated to give 9.1 g of 1-[(phenylhydrazono)(2-fluorophenyl)methyl]-4-phenylpiperazine.

Step 2

To a stirred solution, under nitrogen, of 9.1 g of 1-[(phenylhydrazono)(2-fluorophenyl)methyl]-4-phenylpiperazine in 100 ml of tetrahydrofuran was added, dropwise, a solution of 3.3 g of potassium t-butoxide in 35 ml of tetrahydrofuran. The reaction mixture was stirred at ambient temperature for 4 hours and concentrated. The concentrate was diluted with water and extracted with ethyl acetate. The extract was washed with water, dried over anhydrous magnesium sulfate, and concentrated to a solid. The solid was flash chromatographed on silica gel utilizing hexane/ethyl acetate (30%) as the eluent. Concentration of the appropriate fractions followed by recrystallization from ethyl acetate/hexane gave 2.1 g (25%) of 1-phenyl-3-(4-phenyl-1-piperazinyl)-1H-indazole, mp 129°-130°.

Analysis for $C_{23}H_{22}N_4$: Calculated: 77.93%C; 6.26%H; 15.81%N. Found: 77.91%C; 6.04%H; 15.76%N.

EXAMPLE 6

1-(2-Chlorophenyl)-3-(4-Methyl-1-Piperazinyl)-1H-Indazole Hydrochloride

Step 1

To a stirred solution, under nitrogen, of 89.5 g of 2-chlorophenylhydrazine hydrochloride in 600 ml of pyridine, cooled in an ice bath, was added, dropwise, 87.2 g of 2-fluorobenzoyl chloride, such that the reaction temperature did not exceed 15° C. The reaction mixture was stirred at ambient temperature for 16 hours and then poured into water. Crystallization of the resultant oil was induced by scratching. Recrystallization from toluene yielded 65.7 g (60%) of 2-fluorobenzoic acid, 2-(2-chlorophenyl)hydrazide, m.p. 105°-107° C.

ANALYSIS: Calculated for $C_{13}H_{19}ClFN_2O$: 58.98%C; 3.80%H; 10.58%N. Found: 59.03%C; 3.75%H; 10.56%N.

Step 2

A mixture of 5.2 g of 2-fluorobenzoic acid, 2-(2-chlorophenyl)hydrazide, 64.3 g of triphenylphosphine, 500 ml of anhydrous acetonitrile and 19.3 ml of carbon tetrachloride was stirred at ambient temperature for 16 hours, concentrated in vacuo, and extracted with diethyl ether (4×200 ml). The extract was filtered and concentrated to an oil which, was flash chromatographed on silica utilizing hexane/ethyl acetate (25%) as the eluent. Concentration of the appropriate fractions yielded 47.5 g of α-chloro-2-fluorobenzaldehyde, (2-chlorophenyl)hydrazone.

Recrystallization from hexane afforded the analytical sample, m.p. 36°-38° C.

ANALYSIS: Calculated for $C_{13}H_9Cl_2N_2$: 55.14%C; 3.20%H; 9.90%N. Found: 55,05%C; 3.10%H; 10.17%N.

Step 3

To a stirred solution, under nitrogen, of 10.0 g of α-chloro-2-fluorobenzaldehyde, (2-chlorophenyl)hydrazone was added dropwise, 7.8 g of 1-methylpiperazine. The reaction mixture was stirred at ambient temperature for 2 hrs, cooled, filtered, and concentrated to an oil. Storage at 5° for 16 hrs. solidified the oil. Trituration with hexane gave 9.0 g (74%) of 1-[(2-chlorophenylhydrazono)(2-fluorophenyl)methyl]-4-methylpiperazine. Recrystallization from hexane (2×) afforded the analytical sample, mp 109°-111°.

Analysis for $C_{18}H_{20}ClFN_4$: Calculated: 62.33%C; 5.81%H; 16.15%N. Found: 62.15%C; 5.78%H; 16.27%N.

Step 4

To a stirred solution, under nitrogen of 9.0 g of 1-[(2-chlorophenyl)hydrazono)(2-fluorophenyl)methyl]-4-methylpiperazine in 90 ml of tetrahydrofuran was added, dropwise a solution of 3.5 g of potassium t-butoxide in 40 ml of tetrahydrofuran. The reaction mixture was stirred at ambient temperature for 2 hrs and then concentrated. The concentrate was diluted with water and extracted with ethyl acetate. The extract was washed with water, dried over anhydrous magnesium sulfate and concentrated to give 8.9 g of 1-(2-chlorophenyl)-3-(4-methyl-1-piperazinyl)-1H-indazole as an oil. The oil was dissolved in diethyl ether and treated with ethereal hydrogen chloride to precipitate the hydrochloride salt. The salt was recrystallized from ethanol/diethyl ether (3×) to give 6.1 g (64%) of 1-(2-chlorophenyl)-3-(4-methyl-1-piperazinyl)-1H-indazole hydrochloride, mp 263°-265°.

Analysis for $C_{18}H_{19}ClN_4O$: Calculated: 59.50%C; 5.55%H; 15.42%N. Found: 59.52%C; 5.51%H; 15.31%N.

EXAMPLE 7

1-(2-Chlorophenyl)-3-(1-Piperazinyl)-1H-Indazole Hydrochloride

Step 1

To a stirred solution, under nitrogen, of 30.0 g α-chloro-2-fluorobenzaldehyde, (2-chlorophenyl)hydrazone (prepared as in Step 2 of Example 6) in 300 ml of tetrahydrofuran was added, dropwise, a solution of 36.9 g of ethyl N-piperazinyl carboxylate in 50 ml of tetrahydrofuran. The reaction mixture was stirred at ambient temperature for 16 hours, filtered, and concentrated. The concentrate was diluted with water and then extracted with diethyl ether The extract was washed with water, dried over anhydrous magnesium sulfate and concentrated to yield 46.8 g of 4-[[(2-chlorophenyl)hydrazono](2-fluorophenyl) methyl]-1-piperazine carboxylic acid ethyl ester as an oil.

Step 2

To a stirred solution under nitrogen of 45.2 g of 4-[[(2-chlorophenyl)hydrazono](2-fluorophenyl)methyl]-1-piperazine carboxylic acid ethyl ether in 400 ml of tetrahydrofuran was added, dropwise, a solution of 16.2 g of potassium t-butoxide in 70 ml of tetrahydrofuran. The reaction mixture was stirred at ambient temperature for 16 hours, concentrated in vacuo, diluted with water, and extracted with ethyl acetate. The extract was washed with water, dried over anhydrous magnesium sulfate, and concentrated. The concentrate was flash chromatographed on silica gel eluting with 15% hexane-ethyl acetate. Concentration of the appropriate fractions yielded 34 g (80%) of 4-[1-(2-chlorophenyl)-1H-indazol-3-yl]-1-piperazine carboxylic acid ethyl ester as an oil.

Step 3

A stirred mixture of 28.7 g of 4-[1-(2-chlorophenyl)-1H-indazol-3-yl]-1-piperazine carboxylic acid ethyl ester, 450 ml of 2-methoxymethanol, and a solution of 25 g of potassium hydroxide in 250 ml of water, was refluxed for 16 hours, cooled to ambient temperature, concentrated to about one-third of its volume, poured into water, and extracted with ethyl acetate. The extract was washed with water, dried over anhydrous magnesium sulfate, and concentrated to yield 1-(2-chlorophenyl)-3-(1-piperazinyl)-1H-indazole as an oil. The oil was dissolved in anhydrous diethyl ether and treated with ethereal hydrogen chloride to precipitate the hydrochloride salt. The salt was recrystallized from acetonitrile to yield 18.8 g (72%) of 1-(2-chlorophenyl)-2-(1-piperazinyl)-1H-indazole hydrochloride. Recrystallization from isopropyl alcohol-diethyl ether afforded the analytical sample, m.p. 197°-199°.

ANALYSIS: Calculated for $C_{17}H_{17}N_4Cl·HCl$: 58.46%C; 4.51%H; 16.04%N. Found: 58.54%C; 5.01%H; 15.95%N.

EXAMPLE 8

3-[4-(Dimethylphosphinylmethyl)-1-Piperazinyl]-1-Phenyl-1H-Indazole

A stirred mixture of 4.3 g of 1-phenyl-3-(1-piperazinyl)-1H-indazole (prepared as in Example 2), 2.3 g of potassium carbonate, and 2.3 g of chloromethyldimethylphosphine oxide in 75 ml of dimethylformamide was heated at 90°, under nitrogen, for 16 hrs. Additional chloromethyldimethylphosphine oxide (0.6 g) was added, and the reaction mixture heated at 90° C. for 24 hrs. The reaction mixture was poured into water and the aqueous solution extracted with ethyl acetate. The extract was washed with brine, dried over anhydrous magnesium sulfate and concentrated to an oil. Flash chromatography of the oil on silica gel, eluting with dichloromethane/methanol (10%) followed by concentration of the appropriate fractions and trituration with diethyl ether gave 2.5 g (45%) of 3-[4-(dimethylphosphinylmethyl)-1-piperazinyl)]-1-phenyl-1H-indazole.

Analysis for $C_{20}H_{25}N_4OP$: Calculated: 65.19%C; 6.84%H; 15.21%N. Found: 65.07%C; 6.99%H; 15.08%N.

EXAMPLE 9

4-[1-(4-Fluorophenyl)-1H-Indazol-3-yl]-1-Piperazinecarboxylic Acid Ethyl Ester

Step 1

To a stirred mixture of 80.0 g of 4-fluorophenylhydrazine hydrochloride in 500 ml of dry pyridine, under nitrogen and cooled in an ice bath, was added, dropwise, 85.8 g of 2-fluorobenzoyl chloride. Upon completion of the addition, the ice bath was removed and the reaction mixture stirred at ambient temperature for 16 hours. The reaction mixture was poured into water and a precipitate formed. The precipitate was recrystallized from ethanol-water to give 97.1 g (80%) of 2-fluorobenzoic acid, 2-(4-fluorophenyl)hydrazide.

Analysis: Calculated for $C_{13}H_{10}F_2N_2O$: 62.90%C; 4.06%H; 11.29%N. Found: 62.71%C; 4.12%H; 11.27%N.

Step 2

To a stirred mixture of 79.5 g of 2-fluorobenzoic acid, 2-(4-fluorophenyl)hydrazide in 350 ml of diethyl ether was added, portionwise, 80.0 g of phosphorous pentachloride. Upon completion of the addition, the reaction mixture was refluxed for 1 hr and then stirred at ambient temperature for 16 hrs. In the following order, a solution of 81.3 g of phenol in 80 ml of diethyl ether, 385 ml of methanol, and sufficient water to reach the solution cloud point, were added, dropwise, to the reaction mixture. Upon standing the reaction mixture separated into two layers. The bottom layer was collected, washed with water, and extracted with diethyl ether. The extract was washed with water, dried over anhydrous magnesium sulfate and concentrated to an oil. The oil was purified by flash chromatography on silica gel using 5% ethyl acetate-hexane as the eluent. Evaporation of the appropriate fractions gave 61.5 g of α-chloro-2-fluorobenzaldehyde, (4-fluorophenyl)hydrazone as an oil. Distillation gave the analytical sample bp 144°-155°.

Analysis: Calculated for $C_{13}H_9ClF_2N_2$: 58.55%C; 3.40%H; 10.52%N. Found: 58.44%C; 3.52%H; 10.44%N.

Step 3

To a stirred solution, under nitrogen, of 19.3 g of α-chloro-2-fluorobenzaldehyde, (4-fluorophenyl)hydrazone in 200 ml of tetrahydrofuran was added, dropwise, a solution of 25.2 g of ethyl-1-piperazine carboxylate in 15 ml of tetrahydrofuran. The reaction mixture was stirred at reflux for 45 minutes, cooled and filtered. A solution of 9.7 g of potassium t-butoxide in 110 ml of tetrahydrofuran was added to the stirred filtrate, under nitrogen. Upon completion of the addition, the filtrate was stirred for 2 hours at ambient temperature, and then concentrated. The residue was diluted with distilled water, and extracted with diethyl ether. The extract was washed with water, dried over anhydrous magnesium sulfate and concentrated to yield 27 g of product as a gum. The gum together with a 1.9 g sample of product from a previous run was purified by flash chromatography on silica gel utilizing 40% ethyl acetate-hexane as the eluent. Concentration of the appropriate fractions gave 8.3 g of 4-[1-(4-fluorophenyl)-1H-indazol-3-yl]-1-piperazine carboxylic acid ethyl ester. Recrystallization from isopropyl ether gave the analytical sample, mp 109°–111°.

Analysis: Calculated for $C_{20}H_{25}FN_4O_2$: 65.20%C; 5.75%H; 15.21%N. Found: 65.28%C; 5.46%H; 15.45%N.

EXAMPLE 10

1-(4-Fluorophenyl)-3-(1-Piperazinyl)-1H-Indazole

A stirred solution of 9.2 g of potassium hydroxide in 90 ml of distilled water, 10.0 g of 4-[1-(4-fluorophenyl)-1H-indazol-3-yl]-1-piperazine carboxylic acid ethyl ester, and 180 ml of methoxyethanol was refluxed for 16 hours and then poured into water. The aqueous mixture was extracted with ethyl acetate. The extract was washed with water, dried over anhydrous magnesium sulfate and concentrated to give 6.0 g (75%) of 1-(4-fluorophenyl)-3-(1-piperazinyl)-1H-indazole. Recrystallization from isopropyl ether gave the analytical sample, mp 85°–87°.

Analysis for $C_{17}H_{17}FN_4$: Calculated: 68.90%C; 5.78%H; 18.91%N. Found: 68.82%C; 5.85%H; 18.77%N.

EXAMPLE 11

1-(4-Fluorophenyl)-3-(4-Methyl-1-Piperazinyl)-1H-Indazole Fumarate

To a stirred solution of 8.0 g of α-chloro-2-fluorobenzaldehyde, (4-fluorophenyl)hydrazone in 90 ml of tetrahydrofuran, was added dropwise, a solution of 6.6 g of N-methylpiperazine in 10 ml of tetrahydrofuran. The reaction mixture was refluxed for 45 minutes, cooled, and filtered. A solution of 4.0 g of potassium tert-butoxide dissolved in 45 ml of tetrahydrofuran was added to the stirred filtrate, under nitrogen. Upon completion of addition, the reaction mixture was stirred at ambient temperature for 16 hours, and then concentrated to an oil. The oil was diluted with distilled water and the aqueous mixture extracted with dichloromethane. The extract was washed with distilled water, dried over anhydrous potassium carbonate and concentrated. The residue, together with 2.1 g of impure product from a previous run, was purified on a Water's Model 500 Preparative High Pressure Liquid Chromatograph utilizing two silica gel columns and dichloromethane-methanol (5%) as the eluent. Concentration of the appropriate fractions gave 3.3 g of 1-(4-fluorophenyl)-3-(4-methyl-1-piperazinyl)-1H-indazole as a solid. The solid was dissolved in 150 ml of acetone and 1.2 g of fumaric acid was added with stirring, to give the fumarate salt. Recrystallization of the salt from methanol-diethyl ether yielded 2.4 g (13%) of 1-(4-fluorophenyl)-3-(4-methyl-1-piperazinyl)-1H-indazole fumarate, mp 192°–194°.

Analysis: Calculated for $C_{18}H_{19}FN_4 \cdot C_4H_4O_4$: 61.96%C; 5.44%H; 13.14%N. Found: 61.98%C; 5.46%H; 13.14%N.

EXAMPLE 12

3-(4-Ethyl-1-Piperazinyl)-1-(4-Fluorophenyl)-1H-Indazole Hydrochloride

A mixture of 5.0 g of 1-(4-fluorophenyl)-3-(1-piperazinyl)-1H-indazole, 2.0 g of ethyl bromide, 2.6 g of potassium carbonate and 50 ml of dimethylformamide was heated at 50° C. for 16 hours. The mixture was poured into water and the suspension extracted with ethyl acetate. The ethyl acetate extract was washed with water, dried over anhydrous magnesium sulfate and concentrated to an oil. The oil was diluted with anhydrous diethyl ether and treated with ethereal hydrogen chloride. A precipitate was formed and collected. Recrystallization from ethanol-diethyl ether followed by trituration with refluxing isopropanol gave 3.6 g (59%) of 3-(4-ethyl-1-piperazinyl)-1-(4-fluorophenyl)-1H-indazole hydrochloride, mp 251°–253°.

Analysis for $C_{19}H_{21}FN_4 \cdot HCl$: Calculated: 63.24%C; 6.15%H; 15.53%N. Found: 63.21%C; 6.10%H; 15.49%N.

EXAMPLE 13

3-[4-(2-Propenyl)-1-Piperazinyl]-1-(4-Fluorophenyl)-1H-Indazole Hydrobromide A mixture of 5.0 g of 1-(4-fluorophenyl)-3-(1-piperazinyl)-1H-indazole, 2.6 g of potassium carbonate, 2.2 g of allyl bromide, and 75 ml of dimethylformamide was stirred at 70°–75° for 16 hours, and then at ambient temperature for 48 hours. The mixture was poured into water and the aqueous mixture was extracted with ethyl acetate. The extract was washed with water, dried over anhydrous magnesium sulfate and concentrated to produce an oil. The oil was dissolved in ethyl acetate and a saturated solution of hydrogen bromide in ethyl acetate was added, dropwise, until the solution was acidic. A precipitate was formed and collected. Recrystallization of the precipitate from ethanol gave 2.3 g (33%) of 3-[4-(2-propenyl)-1-piperazinyl]-1-(4-fluorophenyl)-1H-indazole hydrobromide.

Analysis: Calculated for $C_{20}H_{21}FN_4 \cdot HBr$: 57.57%C; 5.32%H; 13.43%N. Found: 57.43%C; 5.46%H; 13.31%N.

EXAMPLE 14

3-[4-(Cyclopropyl)Methyl-1-Piperazinyl]-1-(4-Fluorophenyl)-1H-Indazole Hydrochloride A stirred mixture of 5.0 g of 1-(4-fluorophenyl)-3-(1-piperazinyl)-1H-indazole, 1.6 g of sodium bicarbonate, 1.7 g of chloromethylcyclopropane and 60 ml of dimethylformamide was heated at 85°–90° for 16 hours. Additional chloromethylcyclopropane (0.43 g) was added and the reaction mixture heated at 85°–90° for 8 hrs. The reaction mixture was then poured into water and the aqueous mixture extracted with ethyl acetate. The extract was washed with water, dried over anhydrous magnesium sulfate and concentrated to a solid. The solid was purified by flash chromatography on silica gel utilizing ethyl acetate/diethylamine (3%) as the eluent. Concentration of the appropriate fractions gave 3-[4-(cyclopropyl)methyl-1-piperazinyl]-1-(4-fluorophenyl)-1H-indazole as a solid. The solid was dissolved in anhydrous diethyl ether and treated with ethereal hydrogen chloride to give the hydrochloride salt. The salt was recrystallized from ethanol-diethyl ether (twice) to give 2.6 g (40%) of 3-[4-(cyclopropyl)- methyl-1-piperazinyl]-1-(4-fluorophenyl)-1H-indazole hydrochloride, mp 213°–215°.

Analysis: Calculated for $C_{21}H_{23}FN_4 \cdot HCl$: 65.19%C; 6.25%H; 14.48%N. Found: 64.95%C; 6.54%H; 14.51%N.

EXAMPLE 15

3-(4-Methyl-1-Piperazinyl)-1-[4-(Trifluoromethyl)-phenyl]-1H-Indazole Fumarate

Step 1

To a stirred solution of 75.0 g of 4-(trifluoromethyl)-phenylhydrazine in 500 ml of dry pyridine, cooled in an ice bath, was added dropwise, under nitrogen, 79.1 g of 2-fluorobenzoyl chloride. Upon completion of the addition, the ice bath was removed and the reaction mixture stirred at ambient temperature for 4 hours. The mixture was poured into water and a precipitate formed. Recrystallization of the precipitate from isopropyl alcohol-water, gave 108 g (84%) of 2-fluorobenzoic acid, 2-(4-(trifluoromethyl)phenyl)hydrazide as a solid. Subsequent recrystallization from isopropyl alcohol-water gave the analytical sample, mp 163°–165°.

ANALYSIS: Calculated for $C_{14}H_{10}F_4N_2O$: 56.38%C; 3.38%H; 9.40%N. Found: 56.47%C; 3.19%H; 9.61%N.

Step 2

To a stirred suspension of 95.4 g of 2-fluorobenzoic acid, 2-(4-(trifluoromethyl)phenyl)hydrazide, in 400 ml of anhydrous diethyl ether was added, portionwise, 80.0 g of phosphorous pentachloride. Upon completion of the addition, the reaction mixture was refluxed for 1 hour and then stirred at room temperature for 16 hours. In the following order, a solution of 81.3 g of phenol in 80 ml of diethyl ether, 385 ml of methanol and sufficient water to reach the solution cloud point, were added, dropwise, to the reaction mixture. Upon standing, the reaction mixture separated into two layers. The top layer (aqueous) was extracted with diethyl ether and the extract added to the bottom layer (organic). The combined organic phase was washed with water, dried over anhydrous magnesium sulfate and concentrated to an oil. The oil was purified on a Water's Model 500 High Pressure Liquid Chromatograph using two silica gel columns and 5% ethyl acetate-hexane as the eluent. Concentration of the appropriate fractions gave 79.6 g (78.5%) of α-chloro-2-fluorobenzaldehyde, [4-(trifluoromethyl)phenyl]-hydrazone. Subsequent recrystallization from hexane gave an analytical sample, mp 48°–50°.

ANALYSIS: Calculated for $C_{14}H_9ClF_4N_2$: 53.09%C; 2.86%H; 8.35%N. Found: 53.20%C; 2.84%H; 8.71%N.

Step 3

A solution of 9.5 g of α-chloro-2-fluorobenzaldehyde, [4-(trifluoromethyl)phenyl]hydrazone and 7.2 g of 1-methylpiperazine in 100 ml of tetrahydrofuran was refluxed for 45 minutes, cooled, filtered, and concentrated to an oil. The oil was diluted with water and the aqueous suspension extracted with diethyl ether, dried over anhydrous magnesium sulfate and concentrated to give 10.9 g of 1-[(4-(trifluoromethyl)phenyl)hydrazono)(2-fluorophenyl)methyl]-4-methylpiperazine.

Step 4

To a stirred mixture of 10.8 g of 1-[4-(trifluoromethyl)phenyl)hydrazono) (2-fluorophenyl)methyl]-4-methylpiperazine, 4.7 g of potassium carbonate, and 110 ml of dimethylformamide was stirred at 120° for 65 hours. The reaction mixture was poured into water and the aqueous mixture extracted with ethyl acetate. The extract was washed with water, dried over anhydrous magnesium sulfate and concentrated to an oil. The oil was purified on a Water's Model 500 High Pressure Liquid Chromatograph utilizing two silica gel columns and ethyl acetate-diethylamine (2%) as the eluent. Concentration of the appropriate fractions gave 5.7 g of 3-(4-methyl-1-piperazinyl)-1-[4-(trifluoromethyl)-phenyl]-1H-indazole as a solid. The free base was dissolved in diethyl ether and treated with 3.8 g of fumaric acid. The precipitate was recrystallized (2×) from methanol to give 3.3 g (25%) of 3-(4-methyl-1-piperazinyl)-1-[4-(trifluoromethyl)phenyl]-1H-indazole fumarate, mp 215°–217°.

ANALYSIS: Calculated for $C_{19}H_{19}F_3N_4 \cdot C_4H_4O_4$: 57.98%C; 4.86%H; 11.76%N. Found: 57.95%C; 4.90%H; 11.83%N.

EXAMPLE 16

4-[1-(4-(Trifluoromethyl)Phenyl)-1H-Indazol-3-yl]-1-Piperazine Carboxylic Acid Ethyl Ester

Step 1

To a stirred solution of 25.0 g of α-chloro-2-fluorobenzaldehyde, [4-(trifluoromethyl]phenylhydrazone in 250 ml of tetrahydrofuran was added dropwise, 10.1 g of ethyl-1-piperazinylcarboxylate. The reaction mixture was refluxed for 45 minutes, cooled and filtered. The filtrate was concentrated in vacuo to an oil, which upon trituration with refluxing hexane, gave 31.9 g (92%) of 4-[((4-trifluoromethyl)phenyl))hydrazono) (2-fluorophenyl)methyl]-1-piperazine carboxylic acid ethyl ester as a solid, mp 110°–113°.

Recrystallization from isopropyl ether gave the analytical sample, mp 111°–113°.

ANALYSIS: Calculated for $C_{21}H_{22}F_4N_4O_2$: 57.52%C; 5.06%H; 12.78%N. Found: 57.66%C; 5.05%H; 12.79%N.

Step 2

A stirred mixture of 27.7 g of 4-[(4-trifluoromethylphenyl)hydrazono)(2-fluorophenyl)methyl]-1-piperazine carboxylic acid ethyl ester, 10.5 g of potassium carbonate, and 250 ml of dimethylformamide was heated at 120° for 64 hours. The reaction mixture was poured into water and the aqueous suspension extracted with ethyl acetate. The extract was washed with water, dried over anhydrous magnesium sulfate, and concentrated. The residue was stirred with about 500 ml of hexane for 1 hour, and 21.1 g (80%) of 4-[1-(4-trifluoromethyl)phenyl)-1H-indazol-3-yl]-1-piperazine carboxylic acid ethyl ester collected as a solid, mp 123°–126°. Recrystallization from ethanol/water gave the analytical sample, mp 123°–126°.

ANALYSIS: Calculated for $C_{21}H_{21}F_3N_4O_2$: 60.28%C; 5.06%H; 13.39%N. Found: 60.21%C; 5.08%H; 13.45%N.

EXAMPLE 17

3-(1-Piperazinyl)-1-[4-(Trifluoromethyl)Phenyl]-1H-Indazole Hydrochloride

A stirred solution of 34.0 g of 4-[1-(4-trifluoromethyl)phenyl)-1H-indazol-3-yl]-1-piperazine carboxylic acid ethyl ester, 27.5 g of potassium hydroxide in 275 ml of water, and 550 ml of methoxyethanol was refluxed for 16 hours. The reaction mixture was poured into water and the aqueous suspension extracted with ethyl acetate. The extract was washed with water, dried over anhydrous magnesium sulfate and concentrated in vacuo to give 28 g of 3-(1-piperazinyl)-1-[4-(trifluoromethyl)phenyl]-1H-indazole as a solid. A 4.0 g sample of the free base was dissolved in absolute ethanol and treated with ethereal hydrogen chloride to precipitate the corresponding hydrochloride salt. Recrystallization from ethanol gave 2.2 g (50%) of 3-(1-piperazinyl)-1-[4-(trifluoromethyl)phenyl]-1H-indazole hydrochloride, mp 274°-276°.

ANALYSIS: Calculated for $C_{18}H_{17}F_3N_4 \cdot HCl$: 56.47%C; 4.74%H; 14.64%N. Found: 56.41%C; 4.79%H; 14.74%N.

EXAMPLE 18

3-(4-Ethyl-1-Piperazinyl)-1-[4-(Trifluoromethyl)-Phenyl]-1H-Indazole Fumarate A mixture of 5.0 g of 3-(1-piperazinyl)-1-[4-(trifluoromethyl)phenyl]-1H-indazole hydrochloride, 1.7 g of ethyl bromide, 2.2 g of potassium carbonate, and 50 ml of dimethylformamide was stirred at 50°-55° for 16 hours. The reaction mixture was poured into water and the aqueous mixture extracted with ethyl acetate. The extract was washed with water, dried over anhydrous magnesium sulfate and concentrated to an oil, which solidified upon standing. The solid was dissolved in diethyl ether and treated with 2.8 g of fumaric acid. The resultant salt was then recrystallized from isopropyl alcohol/diethyl ether (2×) to give 2.6 g (38%) of 3-(4-ethyl-1-piperazinyl)-1-[4-(trifluoromethyl) phenyl]-1H-indazole fumarate, mp 194°-197°.

ANALYSIS: Calculated for $C_{20}H_{21}F_3N_4 \cdot C_4H_4O_4$: 58.77%C; 5.14%H; 11.42%N. Found: 58.60%C; 5.20%H; 11.37%N.

EXAMPLE 19

3-[4-(2-Hydroxyethyl)-1-Piperazinyl]-1-[4-(Trifluoromethyl)Phenyl]-1H-Indazole A stirred mixture of 5.5 g of 3-(1-piperazinyl)-1-[4-(trifluoromethyl)phenyl]-1H-indazole hydrochloride, 2.3 g of bromoethanol, 2.5 g of potassium carbonate and 60 ml of dimethylformamide was heated, under nitrogen, at 70°-75° for 16 hours. The reaction mixture was poured into water and the aqueous mixture extracted with ethyl acetate. The extract was washed with water, dried over anhydrous magnesium sulfate and concentrated to an oil. The oil was chromatographed on silica gel utilizing a Water's Model 500 High Pressure Liquid Chromatograph and eluting with dichloromethane/methanol (6%). Evaporation of the appropriate fractions gave an oil which solidified upon standing Recrystallization of the solid from hexane (2×) gave 2.5 g (40%) of 3-[4-(2-hydroxyethyl)-1-piperazinyl]-1-[4-(trifluoromethyl)phenyl]-1H-indazole, mp 82°-84°.

ANALYSIS: Calculated for $C_{20}H_{21}F_3N_4O$: 61.52%C; 5.42%H; 14.35%N. Found: 61.40%C; 5.35%H; 14.32%N.

EXAMPLE 20

3-[4-(Cyclopropyl)Methyl-1-Piperazinyl]-1-[4-(Trifluoromethyl)Phenyl]-1H-Indazole A stirred mixture of 5.0 g of 3-(1-piperazinyl)-1-[4-(trifluoromethyl)phenyl]-1H-indazole hydrochloride, 2.2 g of potassium carbonate, and 1.4 g of chloromethylcyclopropane in 50 ml of dimethylformamide was heated at 85°-90° for 20 hours. The reaction mixture was poured into water and the aqueous suspension extracted with ethyl acetate. The extract was washed with water, dried over anhydrous magnesium sulfate and concentrated to an oil. The oil was flash chromatographed on silica gel utilizing ethyl acetate as the eluent. Concentration of the appropriate fractions gave 2.7 g (48%) of 3-[4-(cyclopropyl)methyl-1-piperazinyl]-1-[4-(trifluoromethyl)phenyl]-1H-indazole, mp 98°-100°.

ANALYSIS: Calculated for $C_{22}H_{23}N_4F_3$: 65.98%C; 5.79%H; 13.99%N. Found: 65.94%C; 5.69%H; 13.92%N.

EXAMPLE 21

3-[4-(2-Phenylethyl)-1-Piperazinyl]-1-[4-(Trifluoromethyl)Phenyl]-1H-Indazole Hydrochloride A stirred mixture of 4.0 g of 3-(1-piperazinyl)-1-[4-(trifluoromethyl)phenyl]-1H-indazole hydrochloride, 2.4 g of (2-bromoethyl)benzene, 1.8 g of potassium carbonate and 60 ml of dimethylformamide was heated, under nitrogen, at 70°-75° for 8 hours, and then stirred at ambient temperature for 8 hours. The reaction mixture was poured into water, and the aqueous mixture extracted with ethyl acetate. The extract was washed with water, dried over anhydrous magnesium sulfate and concentrated to an oil. The oil was chromatographed on a Water's Model High Pressure Liquid Chromatograph utilizing silica columns and eluting with hexane/ethyl acetate (30%). Concentration of the appropriate fractions gave 4.3 g of 3-[4-(2-phenylethyl)-1-piperazinyl]-1-[4-(trifluoromethyl)phenyl]-1H-indazole. The free base was dissolved in diethyl ether and treated with hydrogen chloride to precipitate the corresponding hydrochloride salt. Recrystallization from ethanol/diethyl ether gave 3.1 g of 3-[4-(2-phenylethyl)-1-piperazinyl]-1-[4-(trifluoromethyl) phenyl]-1H-indazole hydrochloride, mp 255°-257°.

ANALYSIS: Calculated for $C_{26}H_{25}F_3N_4 \cdot HCl$: 64.12%C; 5.38%H; 11.51%N. Found: 63.90%C; 5.44%H; 11.605N.

EXAMPLE 22

4-(1-Phenyl-1H-Indazol-3-yl)-1-Piperazine Carbonitrile

To a stirred mixture of 1.5 g of cyanogen bromide 2.0 g of potassium carbonate and 30 ml of dimethylsulfoxide was added, dropwise, a solution of 2.8 g of 1-phenyl-3-(4-methyl-1-piperazinyl)-1H-indazole in 30 ml of dimethylsulfoxide. The reaction mixture was stirred at ambient temperature for 1.5 hours and then poured into water. The aqueous mixture was extracted with ethyl acetate, and the extract was washed with water, dried over anhydrous magnesium sulfate, and concentrated. The concentrate was purified by flash chromatography on silica gel, utilizing ethyl acetate-hexane (1:1) as the eluent, followed by recrystallization from isopropyl alcohol-water to yield 2.3 g (59%) of 4-(1-phenyl-1H-indazol-3-yl)-1-piperazine carbonitrile, m.p. 118°-120°.

ANALYSIS: Calculated for $C_{18}H_{17}N_5$: 71.26%C; 5.65%H; 23.09%H. Found: 71.05%C; 5.67%H; 23.05%N.

EXAMPLE 23

6-Fluoro-1-Phenyl-3-(4-Methyl-1-Piperazinyl)-1H-Indazole Hydrochloride

Step 1

To a stirred mixture, under nitrogen, of 72.3 g of phenylhydrazine hydrochloride in 600 ml of pyridine, cooled in an ice bath, was added, dropwise, 97.1 g of 2,4-difluorobenzoyl chloride, such that the reaction temperature did not exceed 15° C. The reaction mixture was stirred at ambient temperature for about 16 hours. Dilution of the mixture with water formed a precipitate which was collected, dried, and recrystallized from ethyl acetate to yield 98 g (79%) of 2,4-difluorobenzoic acid, 2-phenylhydrazide. Subsequent recrystallization from ethyl acetate afforded the analytical sample, m.p. 171°–173° C.

ANALYSIS: Calculated for $C_{13}H_{10}F_2N_2O$: 62.89%C; 4.06%H; 11.28%N. Found: 62.88%C; 3.98%H; 11.33%N.

Step 2

To a stirred mixture, under nitrogen, of 49.6 g of 2,4-difluorobenzoic acid, 2-phenylhydrazide, 64.3 g of triphenylphosphine, and 500 ml of anhydrous acetonitrile was added 19.3 ml of carbon tetrachloride. The reaction mixture was stirred at ambient temperature for about 16 hours, concentrated, and extracted with diethyl ether (3×). The diethyl ether extract was filtered and concentrated to a residue, which was flash chromatographed on silica gel, eluting first with ethyl acetate-hexane and, in a subsequent run, with ethyl acetate alone. Concentration of the appropriate fractions yielded 47.5 g (89%) of α-chloro-2,4-difluorobenzaldehyde, phenylhydrazone.

Step 3

To a stirred solution of 17.0 g of α-chloro-2,4-difluorobenzaldehyde, phenylhydrazone in 150 ml of tetrahydrofuran was added, dropwise, 14.1 g of 1-methylpiperazine. The reaction mixture was stirred at ambient temperature for 2 hours, filtered, concentrated in vacuo, diluted with water, and extracted with diethyl ether. The extract was washed with water, dried over anhydrous magnesium sulfate and concentrated to yield 19.1 g of 1-[(phenylhydrazono) (2,4-difluorophenyl)methyl]-4-methylpiperazine.

Step 4

To a stirred solution, under nitrogen, 17.0 g of 1-[(phenylhydrazono)(2,4-difluorophenyl)methyl]-4-methylpiperazine in 200 ml of tetrahydrofuran was added dropwise a solution of 7.1 g of potassium t-butoxide in 75 ml of tetrahydrofuran. The reaction mixture was stirred at ambient temperature for 2 hours, then concentrated, diluted with water and extracted with ethyl acetate. The extract was washed with water, dried over anhydrous magnesium sulfate and concentrated to yield 6-fluoro-1-phenyl-3-(4-methyl-1-piperazinyl)-1H-indazole as an oil. The oil was dissolved in ethanol-diethyl ether and treated with ethereal hydrogen chloride to precipitate the hydrochloride salt. Recrystallization from methanol yielded 9.0 g, (45%) of 6-fluoro-1-phenyl-3-(4-methyl-1-piperazinyl)-1H-indazole hydrochloride, m.p. 298°–300°.(dec.).

ANALYSIS: Calculated for $C_{18}H_{19}FN_4 \cdot HCl$: 62.52%C; 5.81%H; 16.15%N. Found: 62.33%C; 5.99%H; 16.28%N.

EXAMPLE 24

1-(2-Fluorophenyl)-3-(4-Methyl-1-Piperazinyl)-1H-Indazole Hydrochloride

Step 1

To a stirred solution, under nitrogen of 35.2 g of 2-fluorophenylhydrazine in 250 ml of dry pyridine, cooled in an ice bath, was added, dropwise, 36.7 ml of 2-fluorobenzoyl chloride. The reaction mixture was stirred at ambient temperature for 21 hours. Upon dilution of the reaction mixture with water a precipitate was formed. Attempts to separate the precipitate by filtration, washing with pyridine, resulted in the formation of an oil. That portion of oil which did not pass into the filtrate was dissolved in dichloromethane and concentrated in vacuo. Upon standing, the filtrate separated into aqueous and organic phases. Treatment of the organic phase with toluene resulted in the formation of a precipitate. Recrystallization of the combined product from toluene yielded 49.2 g of 2-fluorobenzoic acid, 2-(2-fluorophenyl)hydrazide.

Step 2

To a stirred mixture, under nitrogen, of 3.0 g of 2-fluorobenzoic acid, 2-(2-fluorophenyl)hydrazide, 3.0 g of triphenylphosphine, and 25 ml of acetonitrile was added, dropwise, 1.6 g of carbon tetrachloride. The reaction mixture was stirred for 22 hours at ambient temperature and concentrated to an oil. Flash chromatography on silica gel, eluting with 25% ethyl acetate/hexane afforded α-chloro-2-fluorobenzaldehyde, (2-fluorophenyl)hydrazone as an oil.

ANALYSIS: Calculated for $C_{13}H_9N_2ClF_2$: 58.54%C; 3.41%H; 10.51%N. Found: 58.43%C; 3.47%H; 10.29%N.

Step 3

To a stirred solution of 20.2 g of α-chloro-fluorobenzaldehyde, (2-fluorophenyl)hydrazone in 200 ml of tetrahydrofuran was added, dropwise, 16.7 g of N-methylpiperazine. The reaction mixture was stirred at ambient temperature for 16 hours, cooled in an ice bath, and filtered. To the stirred filtrate, under nitrogen, was added, dropwise, a solution of 9.4 g of potassium t-butoxide in 95 ml of tetrahydrofuran. The resulting solution was stirred at ambient temperature for 16 hours and concentrated to a residue, which was then diluted with water and extracted with diethyl ether. The extract was washed with water, dried over anhydrous magnesium sulfate and concentrated to an oil. The oil was purified on a Water's Model 500 Preparative High Pressure Liquid Chromatograph utilizing two silica gel columns and ethyl acetate/diethylamine (2%) as the eluent to yield 17.9 g (76%) of 1-(2-fluorophenyl)-3-(4-methyl-1-piperazinyl)-1H-indazole as an oil. Treatment of a portion of the indazole with ethereal hydrogen chloride produced the corresponding hydrochloride salt. Recrystallization from isopropanol/diethyl ether afforded the analytical sample, m.p. 223°–225°.

ANALYSIS: Calculated for $C_{18}H_{19}FN_4 \cdot HCl$: 62.33%C; 5.81%H; 16.15%N. Found: 62.14%C; 5.81%H; 16.40%N.

EXAMPLE 25

4-(6-Fluoro-1-Phenyl-1H-Indazol-3-yl)-1-Piperazine Carbonitrile

To a stirred mixture of 1.6 g of cyanogen bromide, 2.1 g of potassium carbonate and 30 ml of dimethyl sulfoxide was added, dropwise, a solution of 4.8 g of 6-fluoro-3-(4-methyl-1-piperazinyl)-1-phenyl-1H-indazole in 30 ml of dimethylsulfoxide. The reaction mixture was stirred at ambient temperature for 2 hours and then poured into water. The resulting precipitate was recrystallized from ethanol to yield 2.3 g (48%) of 4-(6-fluoro-1-phenyl-1H-indazol-3-yl)-1-piperazine carbonitrile, m.p. 172°–174°.

ANALYSIS: Calculated for $C_{18}H_{16}FN_5$: 67.27%C; 5.02%H; 21.80%N. Found: 67.01%C; 4.78%H; 21.74%N.

EXAMPLE 26

4-Formyl-1-(1-Phenyl-1H-Indazol-3-yl)Piperazine

To a solution of 3.4 ml of acetic anhydride and 1.5 ml of formic acid heated at 55° C. for 1.5 hours and then cooled to ambient temperature was added, dropwise, a solution of 5.6 g of 1-phenyl-3-(1-piperazinyl)-1H-indazole in 20 ml of tetrahydrofuran. The reaction mixture was stirred at ambient temperature for 2 hours and then concentrated to an oil. Trituration of the oil with refluxing diethyl ether yielded a solid which was recrystallized from isopropanol (3×) to yield 2.6 g (42%) of 4-formyl-1-(1-phenyl-1H-indazol-3-yl)piperazine, m.p. 130°–132°.

ANALYSIS: Calculated for $C_{18}H_{18}N_4O$: 70.57%C; 5.92%H; 18.29%N. Found: 70.68%C; 5.93%H; 18.08%N.

EXAMPLE 27

4-(1-Phenyl-1H-Indazol-3-yl)-1-Piperazine Carboxamide

A mixture of 4.9 g of 1-phenyl-3-(1-piperazinyl)-1H-indazole, 5.1 g of nitrourea, and 80 ml of dimethylformamide was heated on a steam bath for 15 minutes. The reaction mixture was then poured into water and the resulting precipitate was recrystallized from ethyl acetate (2×) to yield 3.1 g (57%) of 4-(1-phenyl-1H-indazol-3-yl)-1-piperazine carboxamide, m.p. 151°–153°.

ANALYSIS: Calculated for $C_{18}H_{19}N_5O$: 67.27%C; 5.96%H; 21.79%N. Found: 66.98%C; 6.04%H; 21.75%N.

EXAMPLE 28

4-[1-(4-Fluorophenyl)-1H-Indazol-3-yl]-1-Piperazine Carboxamide

A mixture of 5.0 g of 1-(4-fluorophenyl)-3-(1-piperazinyl)-1H-indazole, 5.1 g of nitrourea, and 80 ml of dimethylformamide was heated on a steam bath for 15 minutes. The reaction mixture was then poured into water and the resulting precipitate was recrystallized from ethyl acetate (2×) to yield 2.7 g (47%) of 4-[1-(4-fluorophenyl)-1H-indazol-3-yl]-1-piperazine carboxamide, m.p. 148°–150°.

ANALYSIS: Calculated for $C_{18}F_{18}FN_5O$: 63.70%C; 5.34%H; 20.64%N. Found: 63.60%C; 5.34%H; 20.42%N.

EXAMPLE 29

4-[1-(2-Chlorophenyl)-1H-Indazol-3-yl]-1-Piperazine Carboxamide Hemifumarate A mixture of 7.9 g of 1-(2-chlorophenyl)-3-(1-piperazinyl)-1H-indazole, 7.3 g of nitrourea and 100 ml of dimethylformamide was heated on a steam bath for 15 minutes. The reaction mixture was diluted with water and extracted with ethyl acetate. The extract was washed with water, dried over anhydrous magnesium sulfate and concentrated. The concentrate was flash chromatographed on silica gel eluting with chloroform/methanol (5%). Concentration of the appropriate fraction yielded a foam, which when stirred overnight with isopropyl ether afforded 4.0 g of 4-[1-(2-chlorophenyl)-1H-indazol-3-yl]-1-piperazine carboxamide as a powder. A 3.4 g sample of the free base was dissolved in diethyl ether and treated with 1.1 g of fumaric acid. The resulting salt was recrystallized from ethyl acetate to yield 2.3 g (22%) of 4-[1-(2-chlorophenyl)-1H-indazol-3-yl]-1-piperazine carboxamide hemifumarate, m.p. 156°–158°.

ANALYSIS: Calculated for $C_{18}H_{18}ClN_5O \cdot 0.5C_4H_4O_4$: 58.04%C; 4.84%H; 16.92%N. Found: 59.79%C; 4.86%H; 16.94%N.

EXAMPLE 30

4-[1-(4-Trifluoromethyl)Phenyl)-1H-Indazol-3-yl]-1-Piperazine Carboxamide

A mixture of 5.5 g of 3-(1-piperazinyl)-1-[4-(trifluoromethyl)phenyl]-1H-indazole, 4.8 g of nitrourea, and 80 ml of dimethylformamide was heated on a steam bath for 15 minutes. The reaction mixture was then poured into water and the resulting precipitate was collected, washed with water, and dried. The precipitate was purified on a Water's Model 500 Preparative High Pressure Liquid Chromatograph (2×) utilizing two silica gel columns and chloroform/methanol (5%) as the eluent. Concentration of the appropriate fractions yielded a solid which was recrystallized from acetonitrile to afford 2.3 g (37%) of 4-[1-(4-trifluoromethyl)phenyl)-1H-indazol-3-yl]-1-piperazine carboxamide, m.p. 138°–140°.

ANALYSIS: Calculated for $C_{19}H_{18}F_3N_5O$: 58.60%C; 4.66%H; 17.99%N. Found: 58.36%C; 4.65%H; 17.83%N.

EXAMPLE 31

4-(6-Fluoro-1-Phenyl-1H-Indazol-3-yl)-1-Piperazine Carboxamide

A mixture of 4.5 g of 6-fluoro-1-phenyl-3-(1-piperazinyl)-1H-indazole, 4.3 g of nitrourea, and 75 ml of dimethylformamide was heated on a steam bath for 15 minutes. The reaction mixture was then poured into water and the resulting precipitate was recrystallized twice from toluene (one charcoal treatment) to yield 3.5 g (73%) of 4-(6-fluoro-1-phenyl-1H-indazol-3-yl)-1-piperazine carboxamide, m.p. 168°–170°.

ANALYSIS: Calculated for $C_{18}H_{18}FN_5O$: 63.70%C; 5.34%H; 20.64%N. Found: 63.52%C; 5.49%H; 20.50%N.

EXAMPLE 32

1-(2-Fluorophenyl)-3-(1-Piperazinyl)-1H-Indazole Hydrochloride

A mixture of 4-[-(2-fluorophenyl)-1H-indazol-3-yl]-1-piperazine carbonitrile (14.48 g, 0.05 mol) and 25% $H_2SO_4$ (150 ml) was stirred and refluxed for 18 hours. The solution was cooled in an ice bath and was made basic by the dropwise addition of cold 50% aqueous NaOH. The solid that precipitated was collected and washed with cold $H_2O$. The filter cake was dissolved, in $CH_2Cl_2$ solution washed with $H_2O$, dried with $MgSO_4$ and was concentrated to afford 9.0 g of an oil. The oil was dissolved in methanol-ether and ethereal HCl was added to precipitate 8.1 g of the HCl salt. A sample (2.7 g) was triturated with boiling $CH_3CN$, cooled and filtered to give 2.4 g of a powder. The salt was then recrystallized from isopropyl alcohol to afford 1.9 g of 1-(2-fluorophenyl)-3-(1-piperazinyl)-1H-indazole hydrochloride, m.p. 209°-211° C.

ANALYSIS: Calculated for $C_{17}H_{17}FN_4 \cdot HCl$: 61.34%C; 5.46%H; 16.84%N. Found: 61.38%C; 5.45%H; 16.73%N.

EXAMPLE 33

1-(6-Chloro-1-Phenyl-1H-Indazol-3-yl)-1-Piperazine Carbonitrile

To a stirred mixture of 6-chloro-1-phenyl-3-(4-methyl-1-piperazinyl)-1H-indazole (35.7 g, 0.11 mol), $K_2CO_3$ (14.9 g) and dimethylsulfoxide (DMSO) (300 ml) was added, dropwise, BrCN (11.6 g, 0.11 mol) dissolved in DMSO (50 ml). The reaction was stirred at ambient temperature for 2 hours and then it was poured into $H_2O$. The aqueous mixture was extracted with ethyl acetate, however some of the gummy residue solidified upon contact with the ethyl acetate and this was collected The ethyl acetate extract was washed ($H_2O$), dried ($MgSO_4$) and the solvent combined with the material isolated by filtration (5.1 g) to afford 24.2 g of the carbonitrile. The compound was treated with refluxing ethanol-methanol, and after cooling, 19.5 (52%) of solid, 166°-169° C. was collected. An analytical sample was obtained by recrystallization of 4.0 g from ethyl acetate to afford 2.3 g of 1-(6-chloro-1-phenyl-1H-indazol-3-yl)-1-piperazine carbonitrile, m.p. 169°-171° C.

ANALYSIS: Calculated for $C_{18}H_{16}ClN_5$: 63.99%C; 4.77%H; 20.73%N. Found: 63.96%C; 4.77%H; 20.42%N.

EXAMPLE 34

6-Chloro-1-Phenyl-3-(4-Methyl-1-Piperazinyl)-1H-Indazole Fumarate

To a stirred solution of cα-chloro-4-chloro-2-fluorobenzaldehyde, phenylhydrazone (57.5 g, 0.2 mol) in tetrahydrofuran (500 ml), under $N_2$, was added, dropwise, 1-methylpiperazine (44.4 g, 0.44 mol). The reaction was stirred at ambient temperature for 1 hour and then it was filtered to remove 1-methylpiperazine hydrochloride. The filtrate was transferred to a reaction vessel and subsequently potassium t-butoxide (24.7 g, 0.22 mol) dissolved in tetrahydrofuran (250 ml) was added dropwise to the stirred filtrate The reaction was stirred at ambient temperature for 16 hours and then it was concentrated to afford a residue. The residue was diluted with $H_2O$ and the aqueous mixture extracted with ether. The ether extract was washed ($H_2O$), dried ($MgSO_4$), and ethereal HCl added until the mixture was acidic. The resultant hydrochloride salt was then collected and dried to afford 41.5 g of the product. Attempts to recrystallize the hydrochloride salt proved difficult; therefore, the salt was diluted with $H_2O$, stirred and $NH_4OH$ added until the mixture was basic. The resultant free base was extracted into $CH_2Cl_2$, and after washing ($H_2O$) and drying ($K_2CO_3$) and concentrating the extract there remained 38.3 g of the free base as a solid. A portion (5.0 g) of the compound was dissolved in ethyl acetate (100 ml) and fumaric acid (1.2 g, 1 eq) was added and the mixture was heated at reflux for 5 minutes. After stirring at ambient temperature for 16 hours, 5.0 g of a fumarate salt was collected. The salt was recrystallized twice from methanol (with decolorizing carbon) to yield 2.2 g (43%) of 6-chloro-1-phenyl-3-(4-methyl-1-piperazinyl)-1H-indazole fumarate, m.p. 193°-195° C.

ANALYSIS: Calculated for $C_{18}H_{19}ClN_4 \cdot C_4H_4O_4$: 5.58%H; 12.98%N. Found: 59.80%C; 5.58%H; 12.98%N.

EXAMPLE 35

6-Chloro-1-Phenyl-3-(1-Piperazinyl)-1H-Indazole Hydrochloride

A stirred mixture of 4-(6-chloro-1-phenyl-1H-indazol-3-yl)-1-piperazine carbonitrile (9.5 g, 0.028 mol) and 25% aqueous $H_2SO_4$ was refluxed for 16 hours. The reaction mixture was cooled in an ice bath, stirred and then 50% aqueous NaOH was added dropwise until the mixture was basic. The aqueous mixture was extracted with ethyl acetate, the extract washed ($H_2O$), dried ($MgSO_4$) and was concentrated to afford 5.7 g of a solid. A portion (4.1 g) of the solid was dissolved in ether-ethanol and ethereal HCl was added until the mixture was acidic. The resulting insoluble hydrochloride salt was collected and dried to afford 4.4 g of the product. Recrystallization from ethanol twice, with one charcoal treatment) yielded 2.4 g (34%) of 6-chloro-1-phenyl-3-(1-piperazinyl)-1H-indazole hydrochloride, m.p. 271°-273°.

ANALYSIS: Calculated for $C_{17}H_{17}ClN_4 \cdot HCl$: 58.47%C; 5.20%H; 16.05%N. Found: 58.30%C; 5.17%H; 15.93%N.

EXAMPLE 36

1-(4-Methylphenyl)-3-(4-Methyl-1-Piperazinyl)-1H-Indazole Hydrochloride

To a stirred solution, under $N_2$, of α-chloro-2-fluorobenzaldehyde, (4-methylphenyl)hydrazone (22.1 g, 0.09 mol) in tetrahydrofuran (200 ml) was added, dropwise, N-methylpiperazine (27.1 g, 0.27 mol). The solution was allowed to stir at ambient temperature for 3 hours. The solution was cooled in an ice bath for 15 minutes and was then filtered and washed with cold tetrahydrofuran leaving behind the insoluble N-methylpiperazine hydrochloride. The filtrate was concentrated to afford 38.0 g of 1-{[(4-methylphenyl)hydrazono](2-fluorophenyl)methyl}-4-methylpiperazine as a liquid. To a stirred solution of the liquid (38.0 g, 0.12 mol) in tetrahydrofuran (100 ml) was added dropwise, potassium tert-butoxide (11.1 g, 0.10 mol) dissolved in tetrahydrofuran (120 ml). The reaction was allowed to stir at ambient temperature, under $N_2$, for 3.5 hours. The mixture was concentrated to a liquid, and was extracted with ether. The ether was washed ($H_2O$) dried ($MgSO_4$) and was concentrated to afford 24.3 g of a liquid. The liquid was taken up in methanol and ethereal HCl was added to precipitate 18.1 g (60%) of the HCl salt. A 4.9 g sample was recrystallized from CH$_3$CN yielding 2.2 g of 1-(4-methylphenyl)-3-(4-methyl-1-piperazinyl)-1H-indazole hydrochloride, m p. 232°–234° C.

ANALYSIS: Calculated for C$_{19}$H$_{22}$N$_4$·HCl: 66.55%C; 6 77%H; 16.34%N. Found: 66.16%C; 6.78%H; 16.22%N.

EXAMPLE 37

1-(4-Methylphenyl)-3-(1-Piperazinyl)-1H-Indazole Hydrochloride

A mixture of 4-[1-(4-methylphenyl)-1H-indazol-3-yl]-1-piperazine carbonitrile (15.0 g, 0.05 mol) and 25% H$_2$SO$_4$ (150 ml) was stirred and refluxed for 18 hours. The reaction was cooled in an ice bath and made basic by the dropwise addition of 50% aqueous NaOH. The aqueous mixture was extracted with CH$_2$Cl$_2$. The CH$_2$Cl$_2$ was washed with H$_2$O, dried with MgSO$_4$ and concentrated to yield 11.9 g of an oil. The oil was taken up in methanol-ether and ethereal HCl was added to precipitate 10.7 g (70%) of the HCl salt. A 3.3 g sample was recrystallized twice from methanol-ether to afford 2.0 g of 1-(4-methylphenyl)-3-(1-piperazinyl)-1H-indazole hydrochloride, m.p. 250°–252° C.

ANALYSIS: Calculated for C$_{18}$H$_{20}$N$_4$·HCl: 65.73%C; 6.45%H; 17.04%N. Found: 65.16%C; 6.27%H; 16.82%N.

EXAMPLE 38

4-[(2-Fluorophenyl)-1H-Indazol-3-yl]-1-Piperazine Carboxamide Hemifumarate

A solution of 1-(2-fluorophenyl)-3-(1-piperazinyl)-1H-indazole (5.6 g, 0.02 mol), nitrourea (5.1. g, 0.06 mol) and dimethylformamide (100 ml) was warmed on a steam bath for 1.5 hours. The reaction mixture was poured into H$_2$O and the aqueous mixture was extracted with ethyl acetate. The ethyl acetate phase was washed with H$_2$O, dried with MgSO$_4$ and concentrated to 6.9 g of oil. The oil was flash chromatographed over silica gel (300 g) eluting with 10% methanol CH$_2$Cl$_2$. Concentration of appropriate fractions yielded 4.6 g (65%) of a solid which appeared pure on TLC. A 4.4 g sample was dissolved in ethyl acetate (60 ml) and fumaric acid (1.1 eq, 1.3 g) was added. The solution was refluxed for 20 minutes and stirred overnight. The precipitate was collected by filtration and washed with ethyl acetate resulting in 5.1 g of the salt. The salt was recrystallized twice from ethyl acetate to afford 2.0 g (25%) of 4-[1-(2-fluorophenyl)-1H-indazol-3-yl]-1-piperazine carboxamide hemifumarate, m.p. 148°–150° C.

ANALYSIS: Calculated for C$_{18}$H$_{18}$FN$_5$O·0.5C$_4$H$_4$O$_4$: 60.44%C; 5.08%H; 17.62%N. Found: 4.99%H; 17.60%N.

EXAMPLE 39

1-(4-Methoxyphenyl)-3-(4-Methyl-1-Piperazinyl)-1H-Indazole Hydrochloride

To a stirred solution of -chloro-2-fluorobenzaldehyde, 4-methoxyphenylhydrazone (48.0 g, 0.17 mol) and tetrahydrofuran (300 ml) was added dropwise, N-methylpiperazine (2.2 eq, 37.5 g, 0.37 mol). The reaction was allowed to stir under N$_2$ for 19 hours. The reaction mixture was cooled in an ice bath for about 15 minutes, then filtered to remove 1-methylpiperazine hydrochloride. The filtrate was concentrated to 63.7 g of an oil. The oily residue was diluted with H$_2$O, and the aqueous mixture was extracted with ether. The ether was washed with H$_2$O, dried with MgSO$_4$ and concentrated to afford 53.0 g of 1-[[(4-methoxyphenyl)hydrazono](2-fluorophenyl)methyl]-4-methylpiperazine as an oil. To a stirred solution of the oil (53.0 g, 0.15 mol) in tetrahydrofuran (300 ml) was added dropwise potassium tertiarybutoxide (18.7 g, 0.17 mol) dissolved in tetrahydrofuran (300 ml). The reaction was allowed to stir under N$_2$ for 17 hours. The reaction mixture was concentrated to an oil and the oil was partitioned between ether and H$_2$O. The ether phase was dried with MgSO$_4$ and concentrated to yield 45.0 g of a liquid. A 5.0 g sample was purified by preparative HPLC (Water's Associates Prep LC/System 500, 2 silica gel columns, eluting with 5% diethylamine-ethyl acetate) to afford 4.0 g of an oil, which was TLC pure. The oil was taken up in anhydrous ether and ethereal HCl was added to precipitate 3.3 g of the HCl salt. The salt was recrystallized from isopropyl alcohol-ether to afford 2.4 g of 1-(4-methoxyphenyl)-3-(4-methyl-1-piperazinyl)-1H-indazole hydrochloride, m.p. 229°–231° C.

ANALYSIS: Calculated for C$_{19}$H$_{22}$N$_4$O·HCl: 63.58%C; 6.47%H; 15.67%N. Found: 63.46%C; 6.44%H; 15.44%N.

EXAMPLE 40

1-(6-Chloro-1-Phenyl-1H-Indazol-3-yl)-1-Piperazine Carboxamide

A mixture of 6-chloro-1-phenyl-3-(1-piperazinyl)-1H-indazole (5.0 g, 0.016 mol), nitrourea (4.9 g, 0.047 mol) and dimethylformamide (75 ml) was heated on a steam bath for 15 minutes. The reaction was poured into H$_2$O, and the solid that precipitated was collected and dried to afford 5.5 g of the urea. Recrystallization from ethereal H$_2$O (charcoal treatment), and then from dimethylformamide yielded 2.4 g (42%) of 1-(6-chloro-1-phenyl-1H-indazol-3-yl)-1-piperazine carboxamide, m.p. 196° C.

ANALYSIS: Calculated for C$_{18}$H$_{18}$ClN$_5$O: 60.76%C; 5.10%H; 19.68%N. Found: 60.31%C; 5.08%H; 19.35%N.

EXAMPLE 41

4-[1-(4-Methylphenyl)-1H-Indazol-3-yl]-1-Piperazine Carboxamide

A solution of 1-(4-methylphenyl)-3-(1-piperazinyl)-1H-indazole (6.5 g, 0.02 mol), nitrourea (5.9 g, 0.06 mol) and dimethylformamide (150 ml) was warmed on a steam bath for 1.5 hours. The reaction mixture was poured into H$_2$O and the aqueous mixture was extracted with ethyl acetate. The ethyl acetate was washed with H$_2$O, dried with MgSO$_4$ and concentrated to afford 6.8 g of a solid. A 3.8 g sample was purified by preparative HPLC (Water's Associates prep LC/System 500, 2 silica gel columns, eluting with 10% diethylamine-ethyl acetate) to afford 3.6 g of a solid. The solid was recrystallized from toluene to afford 2.5 g of the urea, which occluded toluene. A high vacuum pump was used to remove the residual toluene, while the compound was heated on a steam bath to afford 2.0 g (54%) of 4-[1-(4-methylphenyl)-1H-indazol-3-yl]-1-piperazine carboxamide (54%) m.p. 146°–148° C.

ANALYSIS: Calculated for C$_{19}$H$_{21}$N$_5$O: 68.03%C; 6.32%H; 20.88%N. Found: 68.12%C; 6.71%H; 20.86%N.

EXAMPLE 42

4-[1-(4-Methoxyphenyl)-1H-Indazol-3-yl]-1-Piperazine Carboxamide

A solution of 1-(4-methoxyphenyl)-3-(1-piperazinyl)-1H-indazole hydrochloride (5.0 g, 0.01 mol), nitrourea (4.0 g, 0.04 mol) and dimethylformamide (200 ml) was warmed on a steam bath for 2 hours. The reaction mixture was poured into H$_2$O and the aqueous mixture was extracted with ethyl acetate. The ethyl acetate was dried with MgSO$_4$ and concentrated to 5.3 g of an oil. Crystallization was achieved with toluene affording 3.3 g (65%) of a powder. The powder was recrystallized again from toluene to afford 3.0 g of 4-[1-(4-methoxyphenyl)-1H-indazol-3-yl]-1-piperazine carboxamide, m.p. 155°–157° C.

ANALYSIS: Calculated for C$_{19}$H$_{21}$N$_5$O$_2$: 64.93%C; 6.03%H; 19.93%N. Found: 64.84%C; 6.17%H; 19.82%N.

EXAMPLE 43

1-(4-Methoxyphenyl)-3-(1-Piperazinyl)-1H-Indazole Hydrochloride

A mixture of 4-[1-(4-methoxyphenyl)-1H-indazol-3-yl]-1-piperazine carbonitrile (14.0 g, 0.04 mol) and 25% H$_2$SO$_4$ (130 ml) was stirred and refluxed for 3 hours. The reaction mixture was cooled in an ice bath and made basic by the dropwise addition of 50% aqueous NaOH. The aqueous solution was extracted with CH$_2$Cl$_2$. The CH$_2$Cl$_2$ was washed with H$_2$O, dried with MgSO$_4$ and concentrated to 15.3 g of an oil. The oil was taken up in anhydrous ether and methanol and then ethereal HCl was added to precipitate 12.1 g (88%) of the indazole salt. A 3.5 g sample was recrystallized from ethanol-ether to afford 2.8 g of 1-(4-methoxyphenyl)-3-(1-piperazinyl)-1H-indazole hydrochloride, m.p. 236°–238° C.

ANALYSIS: Calculated for C$_{18}$H$_{20}$N$_4$O·HCl: 62.88%C; 6.15%H; 16.25%N. Found: 62.67%C; 6.17%H; 16.17%N.

EXAMPLE 44

1-(4-Hydroxyphenyl)-3-(4-Methyl-1-Piperazinyl)-1H-Indazole

A mixture of 1-(4-methoxyphenyl)-3-(4-methyl-1-piperazinyl)-1H-indazole (29.0 g, 0.09 mol) and HBr (200 ml) was stirred and refluxed for 2 hours. The mixture was allowed to cool to ambient temperature and H$_2$O (700 ml) was added to precipitate a solid, which was collected by filtration. The solid was washed with a dilute NaHCO$_3$ solution and the resultant powder was collected to afford 24.4 g (70%) of the HBr salt of the compound. The salt proved difficult to purify; therefore, it was converted to the free base and a 7.5 g sample was purified by preparative HPLC (Water's Associates prep LC/System 500, 2 silical gel columns, eluting with 10% methanol/CH$_2$Cl$_2$) to afford 4.5 g of a solid. The compound was recrystallized twice from ethyl acetate to afford 2.8 g of 1-(4-hydroxyphenyl)-3-(4-methyl-1-piperazinyl)-1H-indazole, m.p. 191°–193° C.

ANALYSIS: Calculated for C$_{18}$H$_{20}$N$_4$O: 70.09%C; 6.55%H; 18.17%N. Found: 69.98%C; 6.51%H; 18.17%N.

EXAMPLE 45

4-[1-(4-Methoxyphenyl)-1H-Indazol-3-yl]-1-Piperazine Carbonitrile

To a stirred mixture of BrCN (8.5 g, 0.08 mol), K$_2$CO$_3$ (11.2 g, 0.08 mol) and dimethylsulfoxide (200 ml) under N$_2$, was added, dropwise 1-(4-methoxyphenyl)-3-(4-methyl-1-piperazinyl)-1H-indazole (25.0 g, 0.08 mol) dissolved in dimethylsulfoxide (400 ml). The reaction was allowed to stir at ambient temperature for 18 hours. The reaction was poured into H$_2$O and the aqueous mixture was extracted with ethyl acetate. The ethyl acetate extract was washed with H$_2$O, dried with MgSO$_4$ and concentrated to 22.0 g of a powder (82%). Recrystallization of the compound from isopropyl alcohol gave 17.1 g (64%) of product. A 2.9 g sample was recrystallized again from isopropyl alcohol to afford 2.3 g of 4-[1-(4-methoxyphenyl)-1H-indazol-3-yl]-1-piperazine carbonitrile, m.p. 118°–120° C.

ANALYSIS: Calculated for C$_{19}$H$_{19}$N$_5$O: 68.44%C; 5.76%H; 21.01%N. Found: 68.13%C; 5.74%H; 21.03%N.

EXAMPLE 46

1-(2,4-Dichlorophenyl)-3-(4-Methyl-1-Piperazinyl)-1H-Indazole

To a stirred mixture of α-chloro-2-fluorobenzaldehyde 2,4-dichlorophenylhydrazone (51.0 g, 0.16 mol) and tetrahydrofuran (500 ml) under N$_2$ was added dropwise, 1-methylpiperazine (35.4 g, 0.35 mol). The reaction was allowed to stir for 16 hours and then was cooled in an ice bath for 30 minutes. The mixture was filtered and washed with cold tetrahydrofuran leaving behind the insoluble 1-methylpiperazine hydrochloride. The filtrate was concentrated to afford 72.5 g of 1-{[(2,4-dichlorophenyl) hydrazono](2-fluorophenyl)methyl}-4-methylpiperazine as an oil. To a stirred mixture of the oil (72.5 g, 0.19 mol) and tetrahydrofuran (200 ml), under N2, was added dropwise, potassium tert-butoxide (23.5 g, 0.21 mol) dissolved in tetrahydrofuran (400 ml). The reaction was allowed to stir at ambient temperature for 58 hours. The reaction mixture was concentrated to an oily residue, which was partitioned between ether and H$_2$O. The ether extract was washed with H$_2$O, dried with MgSO$_4$ and concentrated to 58.0 g of an oil. A 9.0 g sample of the oil was flash chromatographed over 500 g silica gel eluting with 20% methanol-CH$_2$Cl$_2$. Concentration of appropriate fractions afforded 5.7 g (55%) of an oil. The oil was dissolved in anhydrous ether and fumaric acid (2.0 g, 1.1 eq) was added. The mixture was stirred overnight and the solid was collected by filtration to afford 4.6 g of product. A 3.8 g sample was recrystallized twice from ethyl acetate to afford 2.2 g of 1-(2,4-dichlorophenyl)-3-(4-methyl-1-piperazinyl)-1H-indazole, m.p. 150°–152° C.

ANALYSIS: Calculated for C$_{18}$H$_{18}$Cl$_2$N$_4$·C$_4$H$_4$O$_4$: 55.35%C; 4.65%H; 11.74%N. Found: 55.12%C; 4.67%H; 11.41%N.

REACTION SCHEME A
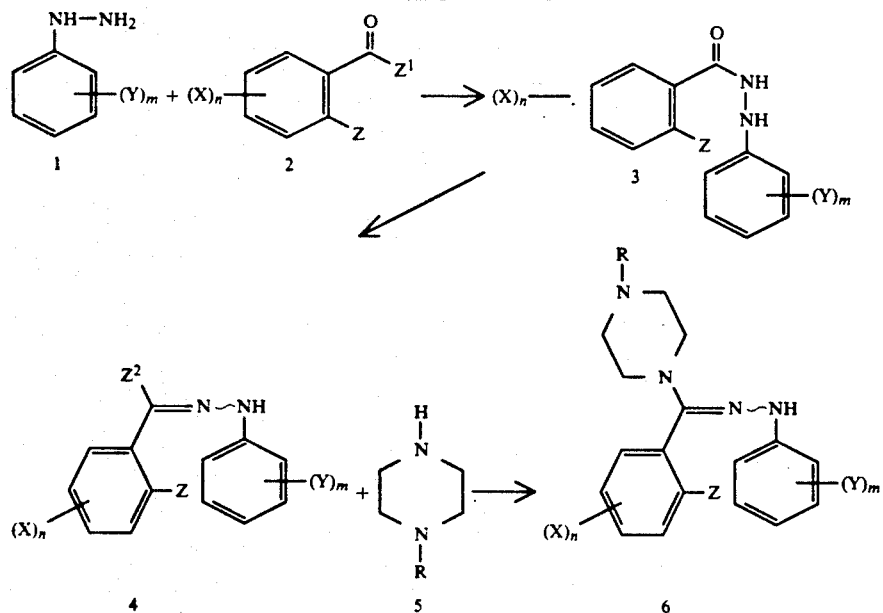
wherein X, Y, n, m and R are as herein described
Z is fluorine or chlorine
$Z^1$ is chlorine or bromine
$Z^2$ is chlorine
REACTION SCHEME B
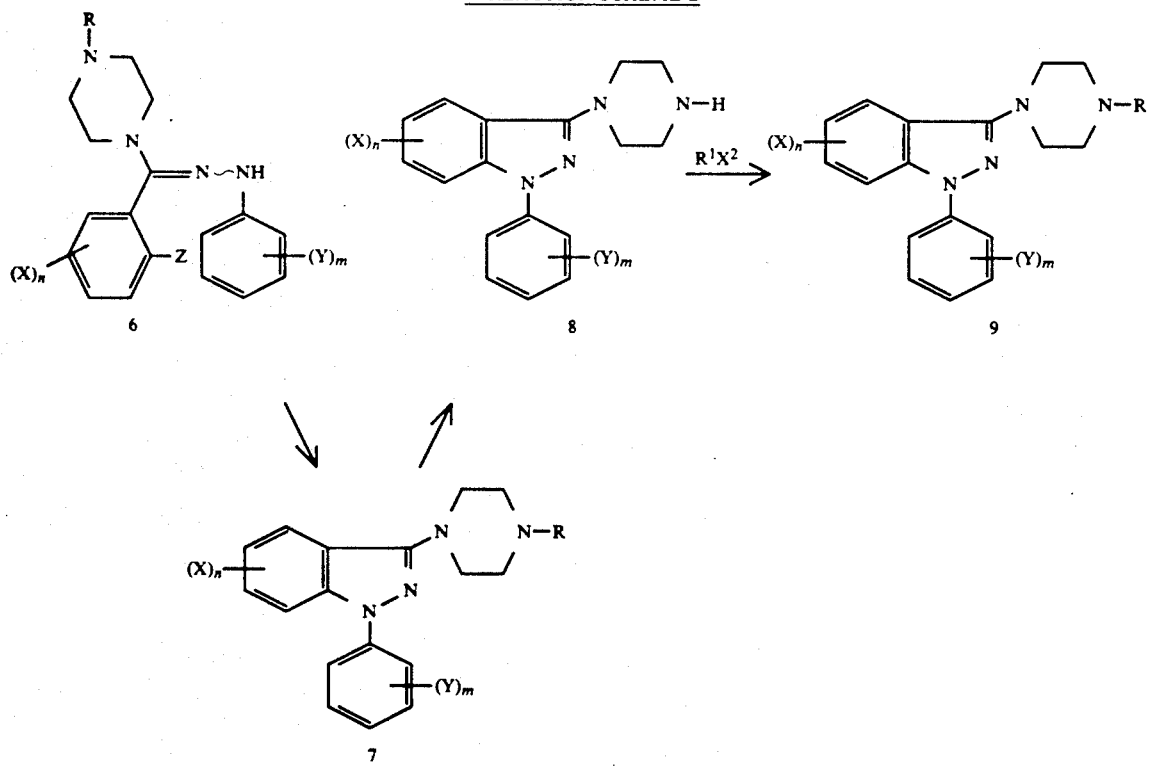
X, Y, n and m are as hereindefined
Z is fluorine or chlorine
R is loweralkyl, loweralkyoxycarbonyl or phenyl
$X^2$ is halogen
$R^1$ is as herein defined

What is claimed is:

1. A compound of the formula:

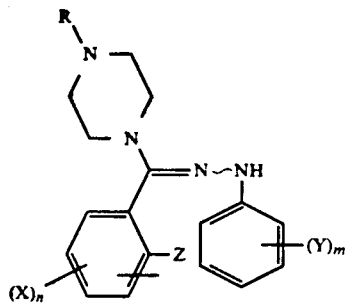

wherein R is selected from the group consisting of loweralkoxycarbonyl, and

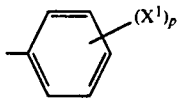

$X^1$ is selected from the group consisting of halogen, loweralkyl, loweralkoxy, loweralkylthio, diloweralkylamino, nitro, cyano, and trifluoromethyl, and p is an integer having a value of 0 to 2 inclusive, wherein for each value of p, $X^1$ may be the same or different; X and Y are independently selected from the group consisting of halogen, loweralkyl, loweralkoxy, loweralkylthio, diloweralkylamino, nitro, cyano, and trifluoromethyl; n is an integer having a value of 0 or 1; m is an integer having a value of 0 to 2 inclusive; wherein for each value of m, Y may be the same or different; and Z is fluorine; the geometrical isomers, optical antipodes, or pharmaceutically acceptable acid addition salts thereof.

2. The compound of claim 1 which is 4-[(phenylhydrazono) (2-fluorophenyl)methyl]-1-piperazine carboxylic acid ethyl ester.

3. The compound of claim 1 which is 4-[(2-chlorophenylhydrazono)(2-fluorophenyl) methyl]-1-piperazine carboxylic acid ethyl ester.

* * * * *